US009322831B2

(12) United States Patent (10) Patent No.: US 9,322,831 B2
Raman et al. (45) Date of Patent: *Apr. 26, 2016

(54) DDX3 AS A BIOMARKER FOR CANCER AND METHODS RELATED THERETO

(71) Applicant: The Johns Hopkins University, Baltimore, MD (US)

(72) Inventors: Venu Raman, Baltimore, MD (US); Guus Martinus Bol, Baltimore, MD (US); Paul Joannes Van Diest, Bilthoven (NL)

(73) Assignee: The Johns Hopkins University, Baltimore, MD (US)

( * ) Notice: Subject to any disclaimer, the term of this patent is extended or adjusted under 35 U.S.C. 154(b) by 158 days.
This patent is subject to a terminal disclaimer.

(21) Appl. No.: 13/840,549

(22) Filed: Mar. 15, 2013

(65) Prior Publication Data

US 2013/0281440 A1 Oct. 24, 2013

Related U.S. Application Data

(63) Continuation-in-part of application No. 13/061,612, filed as application No. PCT/US2009/005273 on Sep. 23, 2009, now Pat. No. 8,518,901, which is a continuation-in-part of application No. PCT/US2012/028475, filed on Mar. 9, 2012.

(60) Provisional application No. 61/099,324, filed on Sep. 23, 2008, provisional application No. 61/450,969, filed on Mar. 9, 2011.

(51) Int. Cl.
*C07D 487/14* (2006.01)
*G01N 33/68* (2006.01)
*G01N 33/574* (2006.01)
*A61K 31/551* (2006.01)

(52) U.S. Cl.
CPC .......... *G01N 33/6893* (2013.01); *A61K 31/551* (2013.01); *C07D 487/14* (2013.01); *G01N 33/57484* (2013.01); *G01N 2333/99* (2013.01)

(58) Field of Classification Search
CPC .................................................. C07D 487/14
See application file for complete search history.

(56) References Cited

U.S. PATENT DOCUMENTS

| | | | |
|---|---|---|---|
| 5,387,585 A | 2/1995 | Borer et al. | |
| 5,698,155 A | 12/1997 | Grosswald et al. | |
| 6,297,245 B1 * | 10/2001 | Shaw | 514/251 |
| 2005/0220796 A1 | 10/2005 | Dynan et al. | |
| 2006/0019268 A1 * | 1/2006 | Cheng et al. | 435/6 |

FOREIGN PATENT DOCUMENTS

WO WO-2010-039187 A2 4/2010

OTHER PUBLICATIONS

Metaye et al. J. of Endocrinology, 2008, vol. 198, pp. 629-631.*
Botlagunta et al. Oncogene, 2008, vol. 27, pp. 3912-3922.*
Sun, Z., et al., "An Improved Synthesis of 9-Benzyladenine: A Model for Adenosine and its Analogues", R.S. Synthetic Communications, vol. 31(4), pp. 549-554. (2001).
Yahya-Zadeh et al., "Synthesis of 5-Amino-1-Aryl-4-Cyanoimidzoles from N-Aryl-N'-(1, 2-Dicyanovinyl)-Formamidines", Synthetic Commununications, vol. 31(21), pp. 3225-3230. (2001).
Dias et al., "Efficient Synthesis of 4,4'-Bi-1H-imidazol-2-ones from 5-Amino-α-imino-1H-imidazole-4-acetonitriles and Isocyanates", Journal Organic Chemistry, vol. 67, pp. 5546-5552. (2002).
Langer, "New Methods of Drug Delivery", Science, vol. 249 No. 4976, pp. 1527-1533. (1990).
Buchwald et al., "Long-Term, Continuous Intravenous Heparin Administration by Implantable Infusion Pump in Ambulatory Patients With Recurrent Venous Thrombosis", Surgery vol. 88 No. 4, pp. 507-516. (1980).
Saudek et al., "A Preliminary Trial of the Programmable Implantable Medication System for Insulin Delivery", New England Journal of Medicine, vol. 321 No. 9, pp. 574-579. (1989).
Langer and Peppas, "Chemical and Physical Structure of Polymers as Carriers for Controlled Release of Bioactive Agents: A Review", Journal of Macromolecular Chemistry and Physics, vol. C23(1), pp. 61-126. (1983).
Levy et al., "Inhibition of Calcification of Bioprosthetic Heart Valves by Local Controlled-Release Diphosphonate", Science, vol. 228, pp. 190-192. (1985).
During et al., "Controlled Release of Dopamine from a Polymeric Brain Implant: In Vivo Characterization", Annals of Neurology, vol. 25 No. 4, pp. 351-356. (1989).
Howard et al., "Intracerebral Drug Delivery in Rats with Lesion-Induced Memory Deficits", Journal of Neurosurgery, vol. 71, pp. 105-112. (1989).
International Search Report, issued in International Application No. PCT/US2009/005273, dated Apr. 23, 2010.
Kumar et al., The First Synthesis of a Novel 5:7:5-Fused Diimidazodiazepine Ring System and Some of its Chemical Properties, Organic Letters, vol. 10, No. 20, pp. 4681-4684 (2008).
International Search Report issued in International Application No. PCT/US2012/028475, dated Sep. 19, 2012.
Extended European Search Report issued in International Application No. PCT/US2009/005273, dated May 24, 2012.
Kondaskar et al., "Novel, Broad Spectrum Anticancer Agents Containing the Tricyclic 5:7:5-Fused Diimidazodiazepine Ring System", ACS Medical Chemistry Letters, vol. 2 No. 3, pp. 252-256. (2010).
Raman, "RNA Helicases: The Next Generation of Targets for Cancer Treatment", Abstracts of the 2010 MIPS Molecular Imaging Seminar Series, available online at http://mips.standford.edu/events/mi_seminar10.html#September, accessed Feb. 7, 2014, p. 6.
Maga et al., Pharmacophore Modeling and Molecular Docking Led to the Discovery of Inhibitors of Human Immunodeficiency Virus-1 Replication Targeting the Human Cellular Aspartic Acid#Glutamic Acid#Alanine#Aspartic Acid Box Polypeptide 3, Journal of Medicinal Chemistry, vol. 51, pp. 6635-6638. (2008).
Miao et al., Mectin-2 and DDX3 are Biomarkers for Metastasis and Poor Prognosis of Squamous Cell/AdenoSquamous Carcinomas and AdenoCarcinoma of Gallbladder, International Journal of Clinical Experimental Pathology, vol. 6(2), pp. 179-190. (2013).
Högbom et al., "Crystal Structure of Conserved Domains 1 and 2 of the Human DEAD-box Helicase DDX3X in Complex with the Mononucleotide AMP", Journal of Molecular Biology, vol. 372, pp. 150-159. (2007).

* cited by examiner

*Primary Examiner* — Samira Jean-Louis

(74) *Attorney, Agent, or Firm* — Venable LLP; Keith G. Haddaway; Annette K. Kwok

(57) ABSTRACT

The invention encompasses methods for treating or preventing diseases and disorders associated abnormal cell growth, for example, treating or preventing cancer or tumor growth, by administering to a subject in need thereof a composition comprising a therapeutically or prophylactically effective amount of a compound that downregulates DDX3, for example a fused diimidazodiazepine ring compound or a pharmaceutically acceptable salt thereof. The invention also encompasses the use of DDX3 as a biomarker for diagnostic and treatment purposes, for example, to identify a hyperproliferative disorder susceptible to treatment by down regulation of DDX3.

22 Claims, 26 Drawing Sheets

Normal lung cell line

Leukemia Cell Lines

Prostate cancer cell line

FIG. 23
Normal    Carcinoma
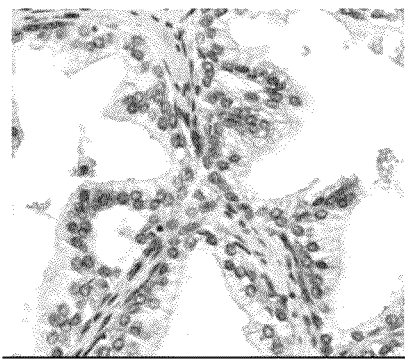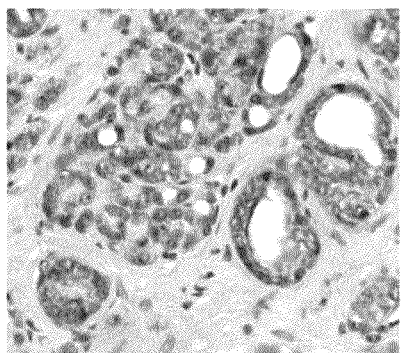
FIG. 24
chondrosarcoma    Pleomorphic sarcoma
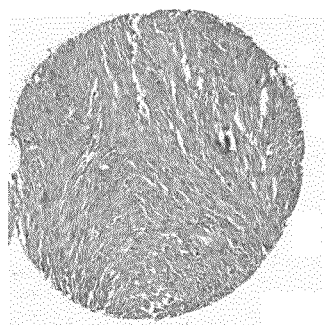

FIG. 25
Normal brain
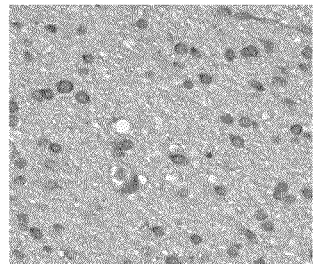
Glioblastoma
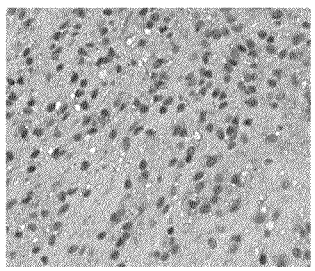
Medulloblastoma
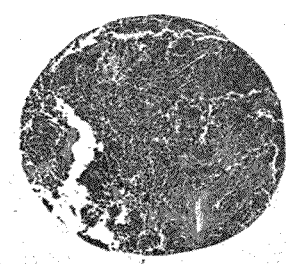

Immunoblot analyses for DDX3 expression in lung, prostate and glioblastoma cell lines

FIG. 27
Figure 11
Cerebellum-
Brain
Control　　　　　　　　Treated
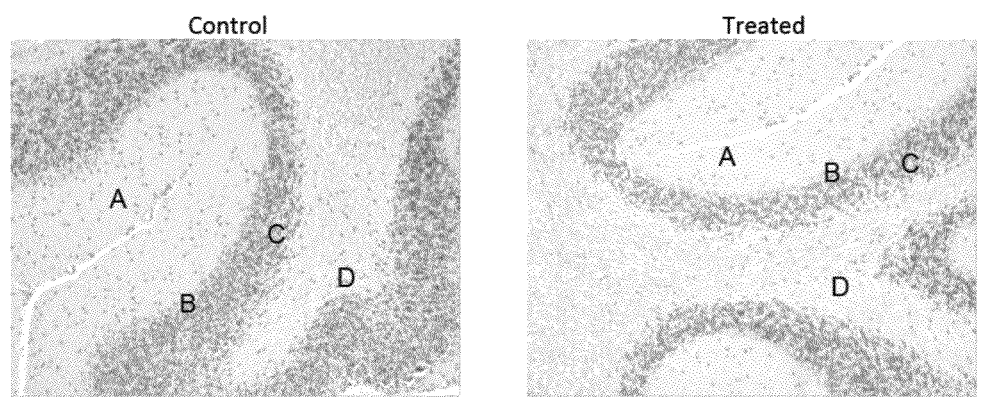
A-Molecular layer
B-Purkinje cells
C-Granular cell layer
D-White matter
Similar patterns in both groups
FIG. 28
Control　　　　　　　　Treated
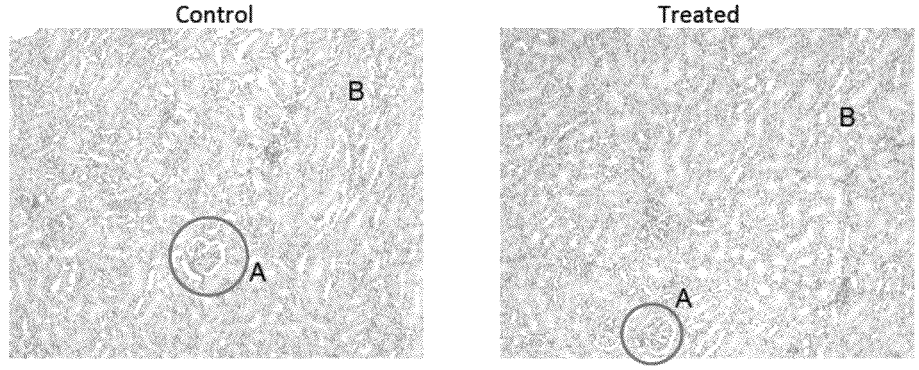
Kidney
A-glomerulus
B-tubules
Similar patterns in both groups Liver Centrilobular area circled- similar patterns in both groups Spleen   Red (pink) and White (blue) Pulp similar patterns in both groups Blood smear A-monocytes, B-Platelet, C-Neutrophils, D-RBC Similar patterns, cell numbers and types in both blood smears

DDX3 AS A BIOMARKER FOR CANCER AND METHODS RELATED THERETO

This application is a continuation-in-part of U.S. application Ser. No. 13/061,612, which is a 371 National Stage of PCT International Application No. PCT/US2009/05273, filed Sep. 23, 2009, which claims the benefit of U.S. provisional patent application No. 61/099,324, filed Sep. 23, 2008, the disclosures of which are incorporated herein by reference in their entirety. This application is also a continuation-in-part of PCT International Application No. PCT/US2012/028475, filed Mar. 9, 2012, which claims the benefit of U.S. provisional patent application No. 61/450,969, filed Mar. 9, 2011, the disclosures of which are incorporated herein by reference in their entirety.

FIELD OF THE INVENTION

The invention encompasses methods for identifying hyperproliferative disorders and subjects having hyperproliferative disorders treatable by downregulation of DDX3 by determining expression of DDX3 in tissues and cells. The invention also encompasses methods of treating hyperproliferative disorders by administering a compound that downregulates DDX3 to a subject having a hyperproliferative disorders that overexpresses DDX3. The invention also encompasses methods for treating or preventing cancer, tumors and other disorders associated abnormal cell growth by administering to a subject in need thereof a composition comprising a therapeutically or prophylactically effective amount of a compound that downregulates DDX3. The invention also encompasses methods for treating hyperproliferative disorders using compounds having a fused diimidazodiazepine ring system that downregulates DDX3.

BACKGROUND OF THE INVENTION

Treatment of cancer varies based on the type of cancer and its stage. The stage of a cancer refers to how much it has grown and whether the tumor has spread from its original location. If the cancer is confined to one location and has not spread, the most common goals for treatment are surgery and cure. This is often the case with skin cancers, as well as cancers of the lung, breast, and colon.

If the tumor has spread to local lymph nodes only, sometimes these can also be removed. If surgery cannot remove all of the cancer, the options for treatment include radiation, chemotherapy, or both. Some cancers require a combination of surgery, radiation, and chemotherapy.

Although current radiotherapeutic agents, chemotherapeutic agents and biological toxins are potent cytotoxins, they do not discriminate between normal and malignant cells, producing adverse effects and dose-limiting toxicities. There remains specific cancer markers and identifying cancers, tumors and other disorders associated abnormal cell growth that can be treated with drugs that are effective for treating such disorders without producing adverse effects and dose-limiting toxicities to normal cells.

Surprisingly, the methods and compositions of the invention fulfill the needs and satisfy other objects and advantages that will become apparent from the description which follows.

SUMMARY OF THE INVENTION

The present invention relates to methods of treating cancer and other hyperproliferative disorders using compounds that are effective in discriminately inhibiting the growth of cancer and tumor cells by downregulation of DDX3 while allowing healthy "normal" cells to remain unaffected. The present invention also relates to methods for identifying cancers, tumors and other hyperproliferative disorders associated with abnormal cell growth treatable by the specifically described compounds and others.

The invention encompasses methods of treatment by administering compounds that downregulate expression of DDX3, including the compounds of Formulas I-V, that are useful for treating or preventing a disease or disorder including, but not limited to, conditions caused by uncontrolled cell growth, hyperproliferation of cells, tumor growth, and cancers.

The invention also encompasses methods for treating or preventing pancreatic cancer, liver cancer, ovarian cancer, breast cancer; lung cancer; prostate cancer; brain cancer including glioblastoma, medulloblastoma, and pontine tumors; kidney cancer; leukemia; or a sarcoma, which comprises administering to a mammal in need of such treatment or prevention a therapeutically or prophylactically effective amount of a composition comprising a compound of Formula I-V, or a pharmaceutically acceptable salt or prodrug thereof, and a pharmaceutically acceptable vehicle.

DDX3, a member of a RNA helicase family, is dysregulated in many cancer types including, breast cancer; lung cancer; prostate cancer; brain cancer including glioblastoma, medulloblastoma, and pontine tumors; kidney cancer; leukemia; and a sarcomas. The present invention provides that that targeted downregulation of the expression of DDX3, using a small molecule inhibitor, for example a fused diimidazodiazepine, is effective on lung cancer cell lines including a carboplatin resistant cell line.

In accordance with an embodiment, the present invention provides that compounds, for example a fused diimidazodiazepine compound according to the invention, or a salt, solvate, stereoisomer, or derivative thereof, and a pharmaceutically acceptable carrier, acting as a DDX3 inhibitor in a mammalian cell or population of cells in a subject suffering from a proliferative disease are useful in treating the hyperproliferative disorder.

In accordance with another embodiment, the present invention provides a method of treating cancer in a subject comprising administering to the subject an effective amount of a composition comprising a compound that is a DDX3 inhibitor, for example, a fused diimidazodiazepine compound according to the invention, or a salt, solvate, stereoisomer, or derivative thereof, and a pharmaceutically acceptable carrier.

The invention includes a method of treating a hyperproliferative disorder susceptible to treatment by downregulation of DDX3 by administering to a subject in need thereof an effective amount of a composition or formulation comprising a compound that downregulates DDX3. Compounds that downregulate DDX3 include compounds of Formula (I):

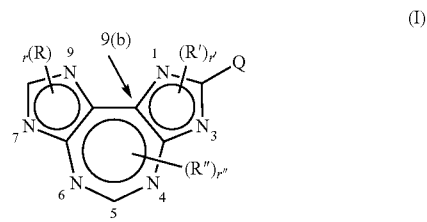

or pharmaceutically acceptable salts and prodrugs thereof, as described further below. A specific compound is

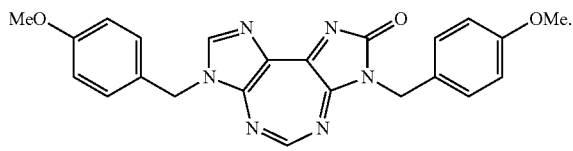 [SMILES: COc1ccc(Cn2c3ncnc4c(ncn4Cc4ccc(OC)cc4)c-3nc2=O)cc1]

The hyperproliferative disorder can be, for example breast cancer, lung cancer, prostate cancer, glioblastoma, kidney cancer. leukemia, medulloblastoma, pontine tumors, or a sarcoma. Specific disorders include breast cancer, lung cancer, prostate cancer or glioblastoma. The sarcoma can be, for example, chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS).

The invention is also a method of identifying a subject having a hyperproliferative disorder susceptible to treatment by down regulation of DDX3. The method includes the steps of obtaining a cell or tissue sample from tissue of the subject associated with or suspected to be associated with the disorder; optionally isolating cells from the tissue; measuring expression of DDX3 in the tissue or in the cells isolated from the tissue; and identifying the subject as having the hyperproliferative disorder as susceptible to treatment by down regulation of DDX3 if DDX3 is expressed in the tissue or cell sample. The hyperproliferative disorder can be, for example, breast cancer; lung cancer; prostate cancer; brain cancer including glioblastoma, medulloblastoma, and pontine tumors; kidney cancer; leukemia; or a sarcoma. In some embodiments, the hyperproliferative disorder is breast cancer, lung cancer, prostate cancer or glioblastoma. In other embodiments the hyperproliferative disorder is breast cancer. In embodiments, the hyperproliferative disorder is lung cancer. Measuring DDX3 expression can be accomplished by immunohistochemistry analysis of the tissue sample. Measuring DDX3 expression also can be accomplished by isolating cells from the tissue sample and measuring expression of DDX3 in the tissue by measuring expression of DDX3 in the cells. The method can include the steps of performing an assay by exposing cells to a compound that downregulates DDX3, measuring cell viability as a function of concentration and identifying the hyperproliferative disorder as susceptible to treatment by down regulation of DDX3 if cell viability decreases as a function of concentration. The assay can be a MTS assay. The compound that deregulates DDX3 expression can be a compound of Formula (I) as described herein, for example:

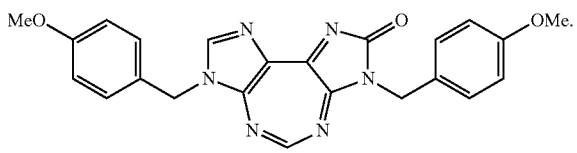 [SMILES: COc1ccc(Cn2c3ncnc4c(ncn4Cc4ccc(OC)cc4)c-3nc2=O)cc1]

The present invention may be understood more fully by reference to the figures, detailed description, and examples, which are intended to exemplify non-limiting embodiments of the invention.

BRIEF DESCRIPTION OF THE DRAWINGS

FIG. 9A) qRT-PCR of DDX3 levels in a series of immortalized normal breast cell lines (1-2) and breast cancer cell lines (3-7). The breast cancer cell lines are in the order of aggressive phenotype. FIG. 9B) Immunoblot analysis for DDX3 expression in the identical cell lines as above.

Figure 16:
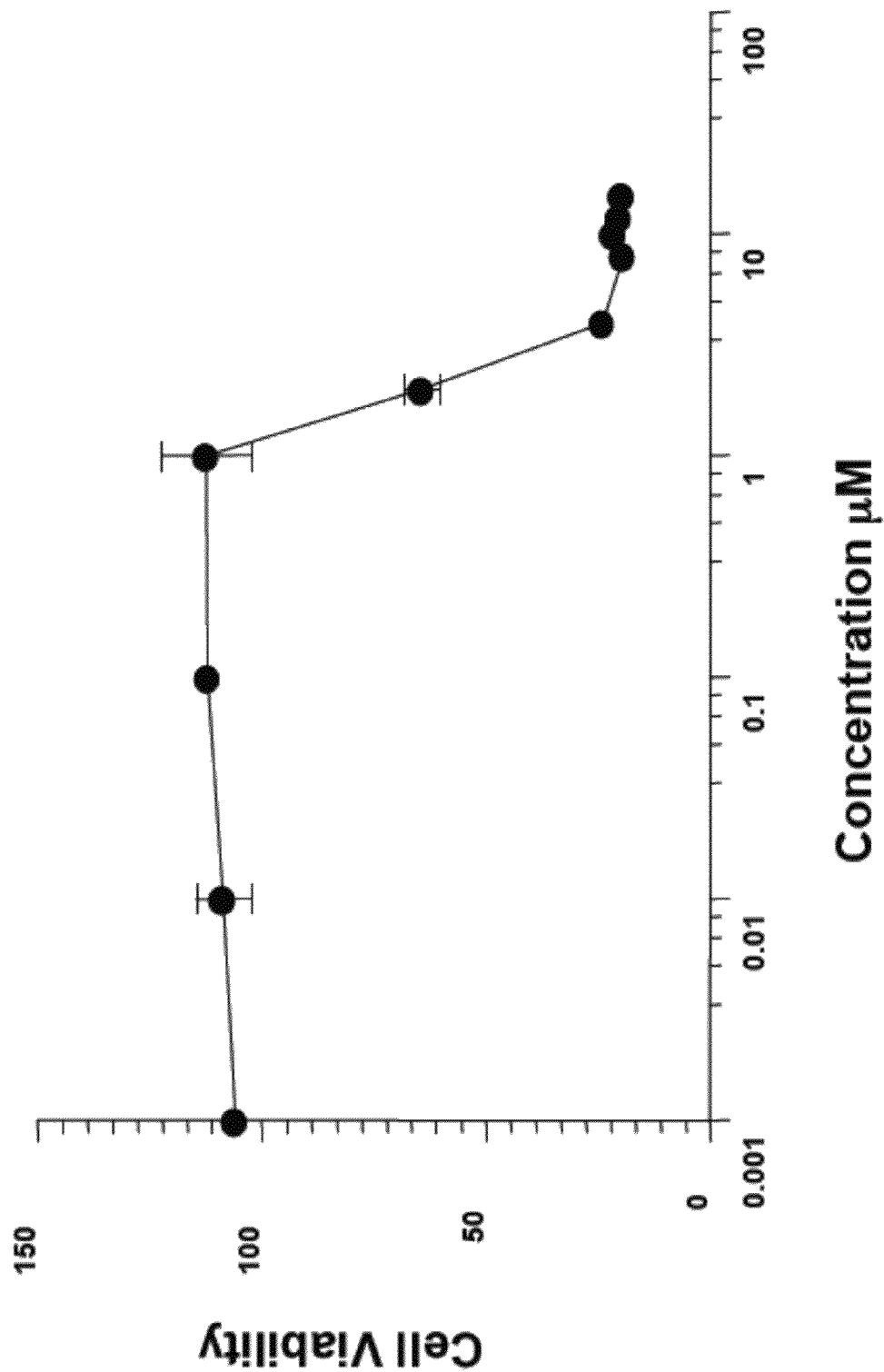
Figure 17:
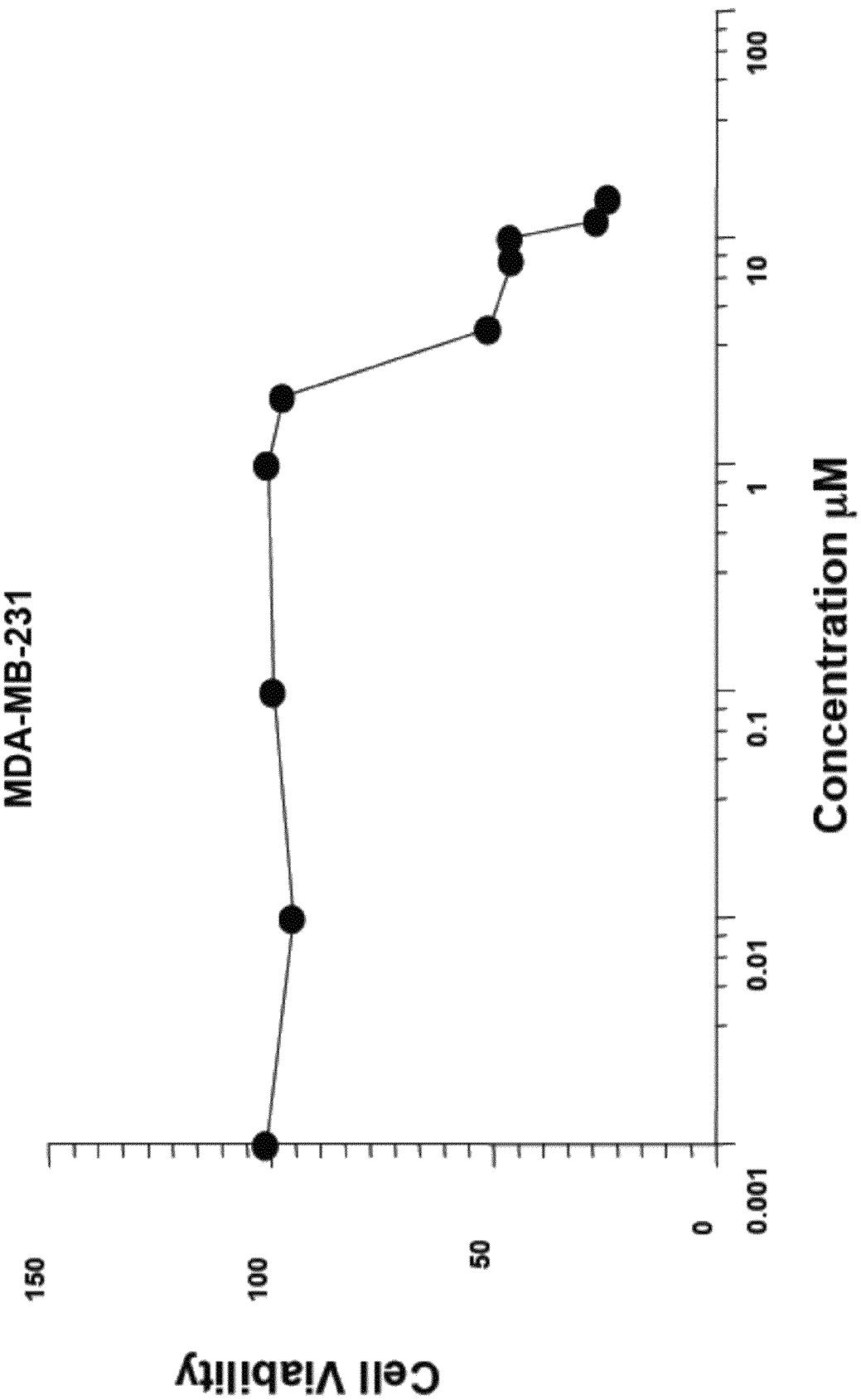
Figure 18:
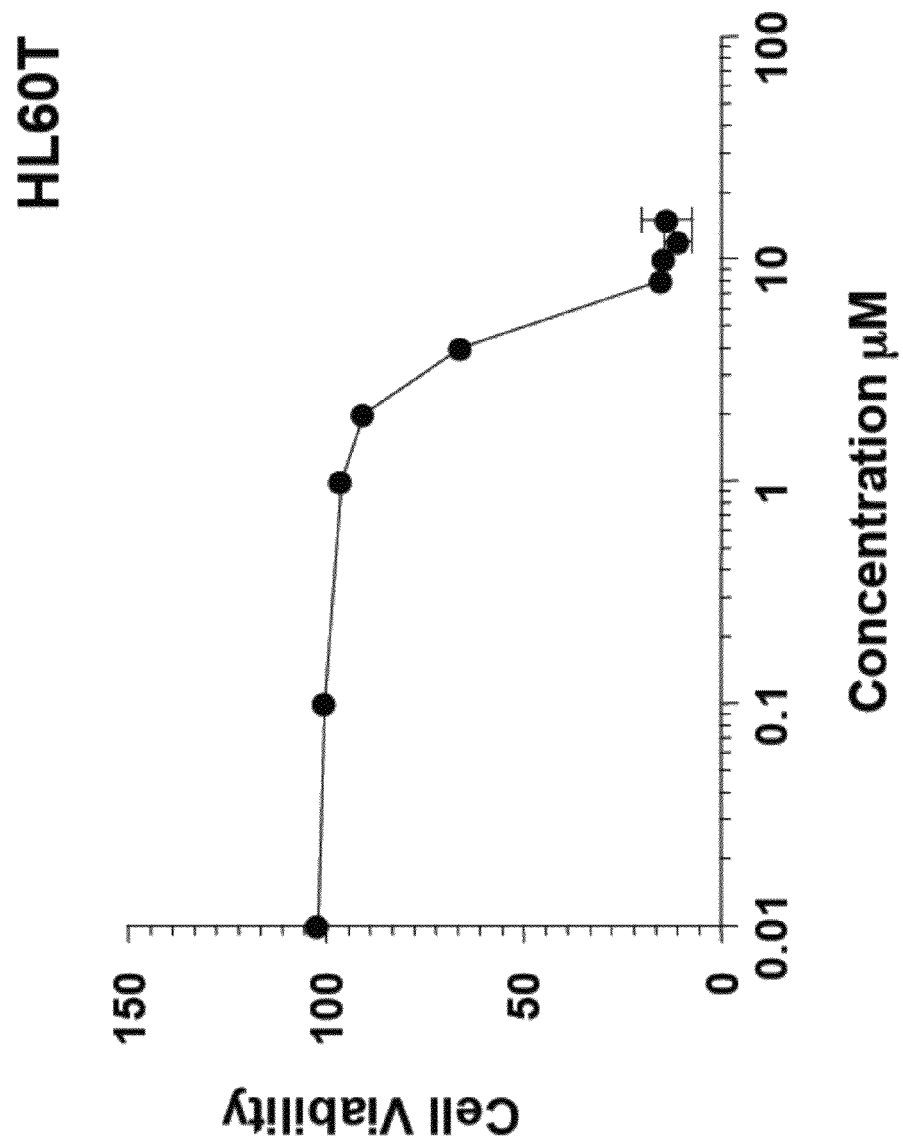

X-axis indicates concentration of drug used. The cells were incubated for three days (fresh drug was added daily) following which cell viability was determined;

FIG. 16 illustrates MTS assays of MDA-MB-468 cells (breast cancer cell line) incubated with Compound 3 of the invention. X-axis indicates concentration of drug used. The cells were incubated for three days (fresh drug was added daily) following, which cell viability was determined;

FIG. 17 illustrates MTS assays of MDA-MB-231 cells (breast cancer cell line) incubated with Compound 3 of the invention. X-axis indicates concentration of drug used. The cells were incubated for three days (fresh drug was added daily) following which cell viability was determined;

FIG. 18 illustrates MTS assays of HL60T cells (leukemia cell line) incubated with Compound 3 of the invention. X-axis indicates concentration of drug used. The cells were incubated for three days (fresh drug was added daily) following which cell viability was determined.

Figure 19:
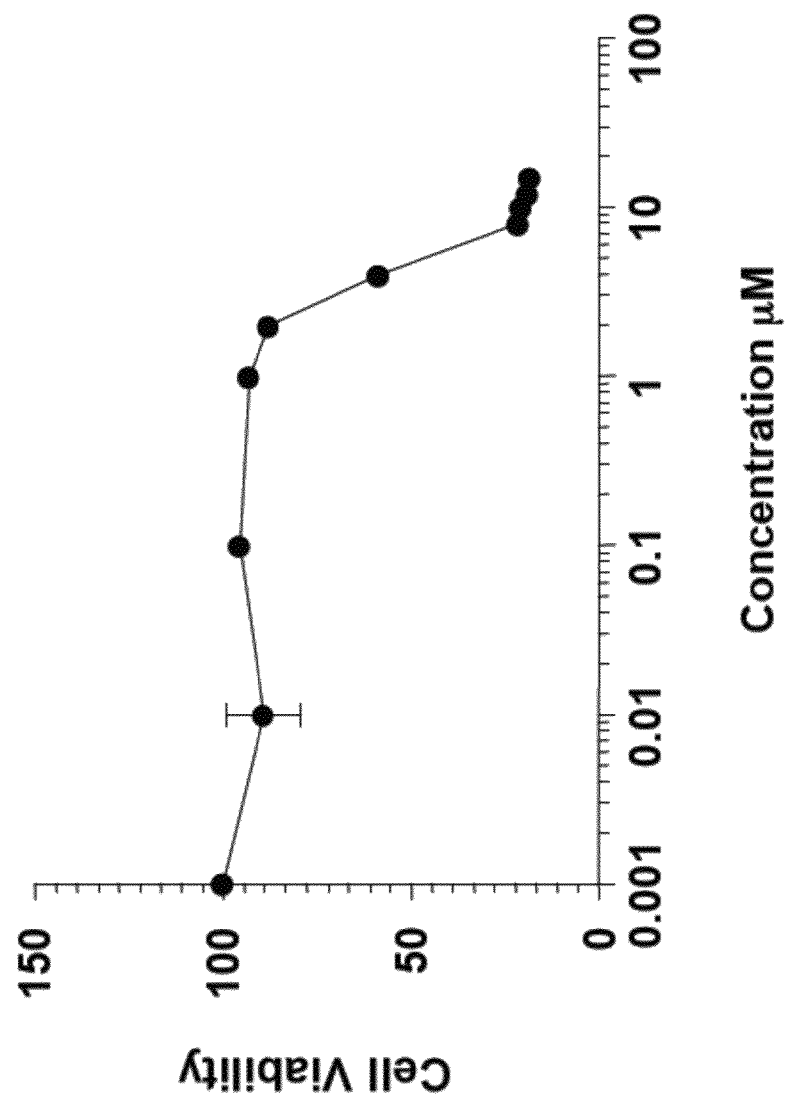

FIG. 19 illustrates MTS assays of HNT34 cells (leukemia cell line) incubated with Compound 3 of the invention. X-axis indicates concentration of drug used. The cells were incubated for three days (fresh drug was added daily) following which cell viability was determined.

Figure 20:
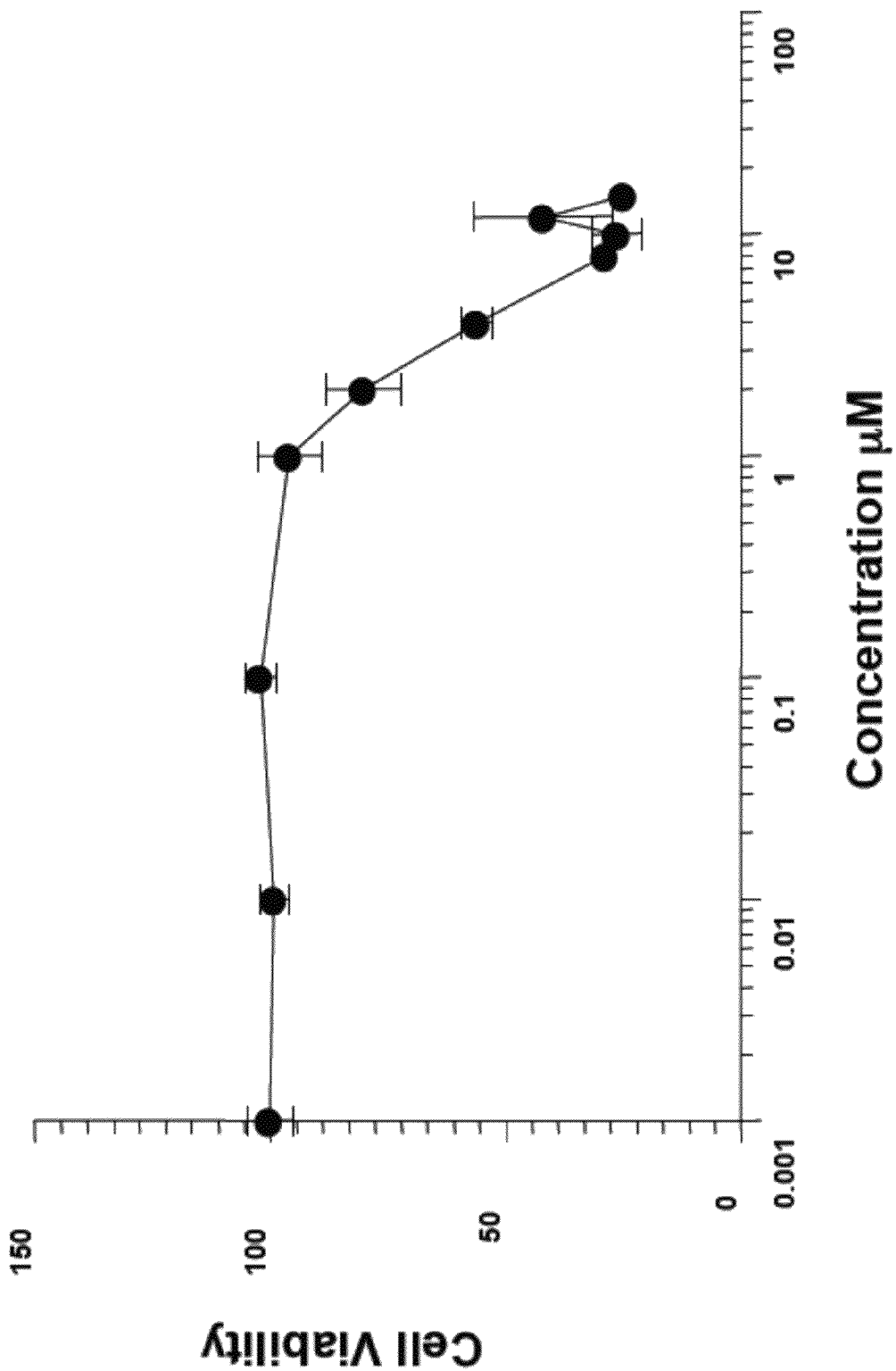

FIG. 20 illustrates MTS assays of KG101 cells (leukemia cell line) incubated with Compound 3 of the invention. X-axis indicates concentration of drug used. The cells were incubated for three days (fresh drug was added daily) following which cell viability was determined.

Figure 21:
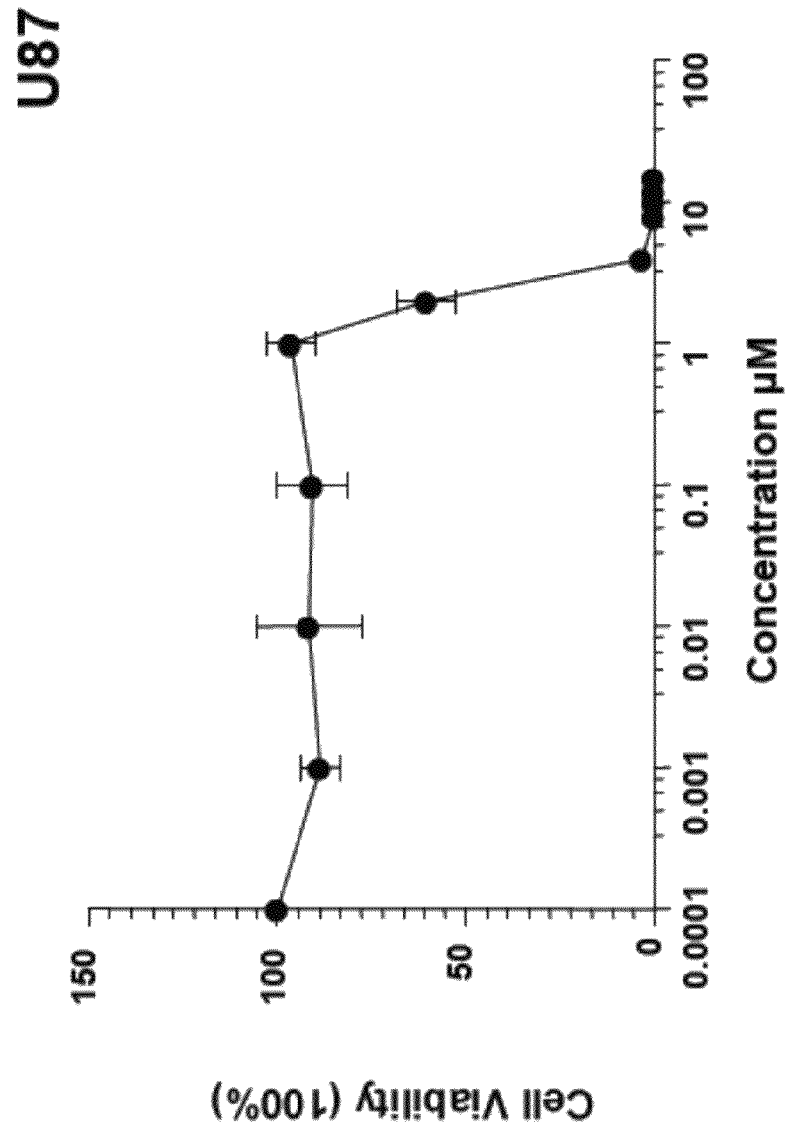
Figure 22:
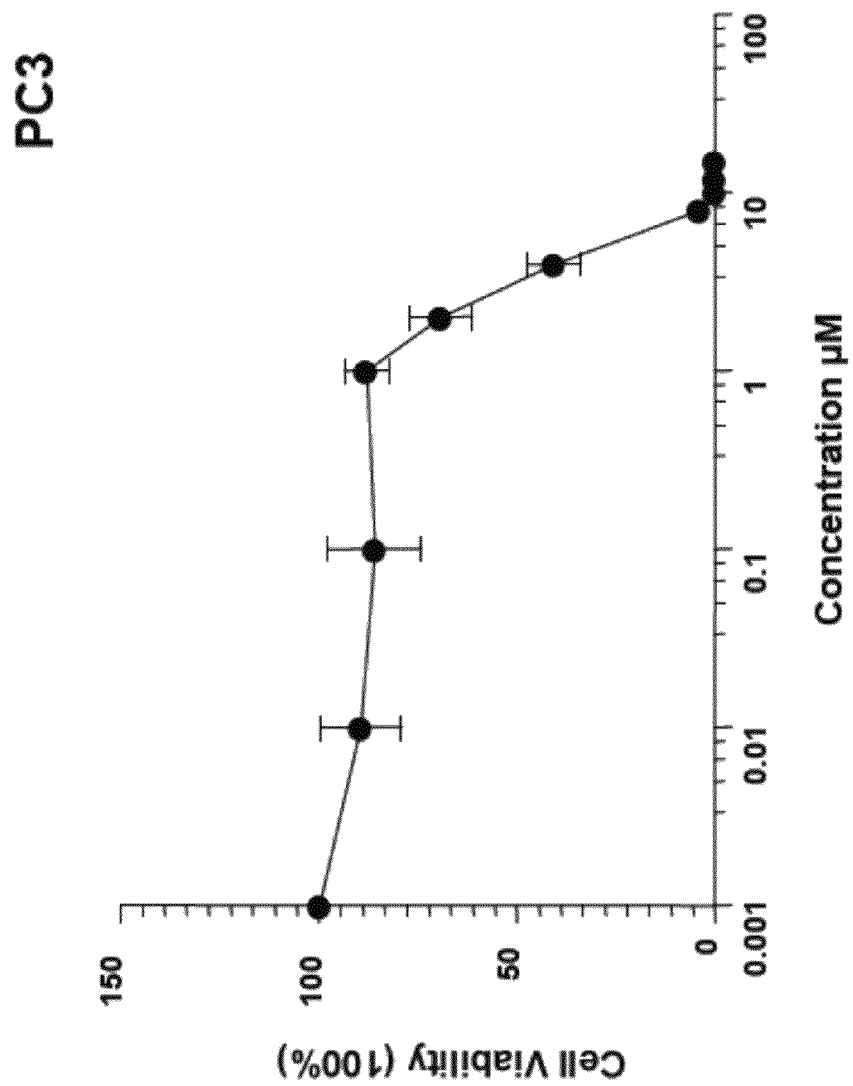
Figure 26:
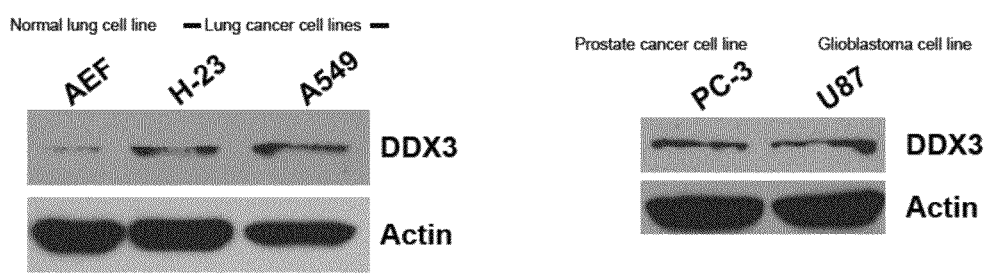
Figure 29:
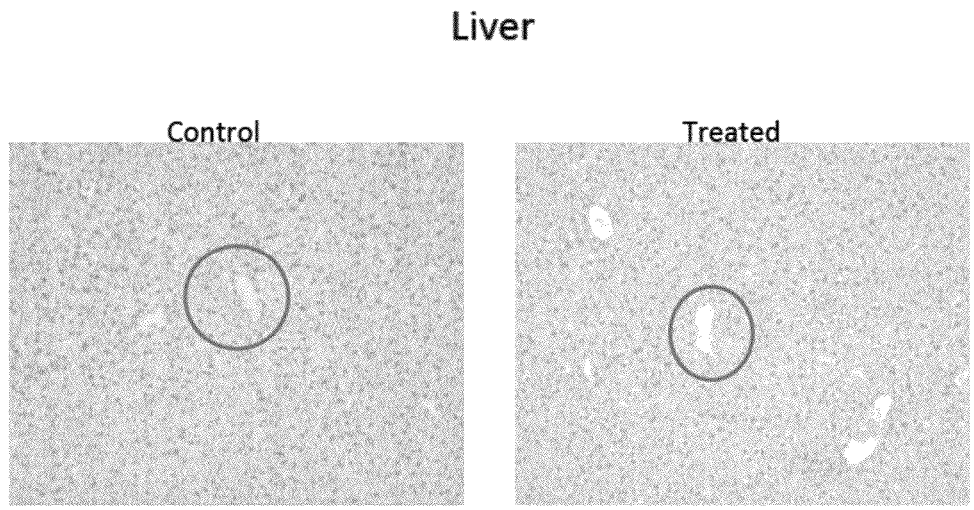
Figure 32:
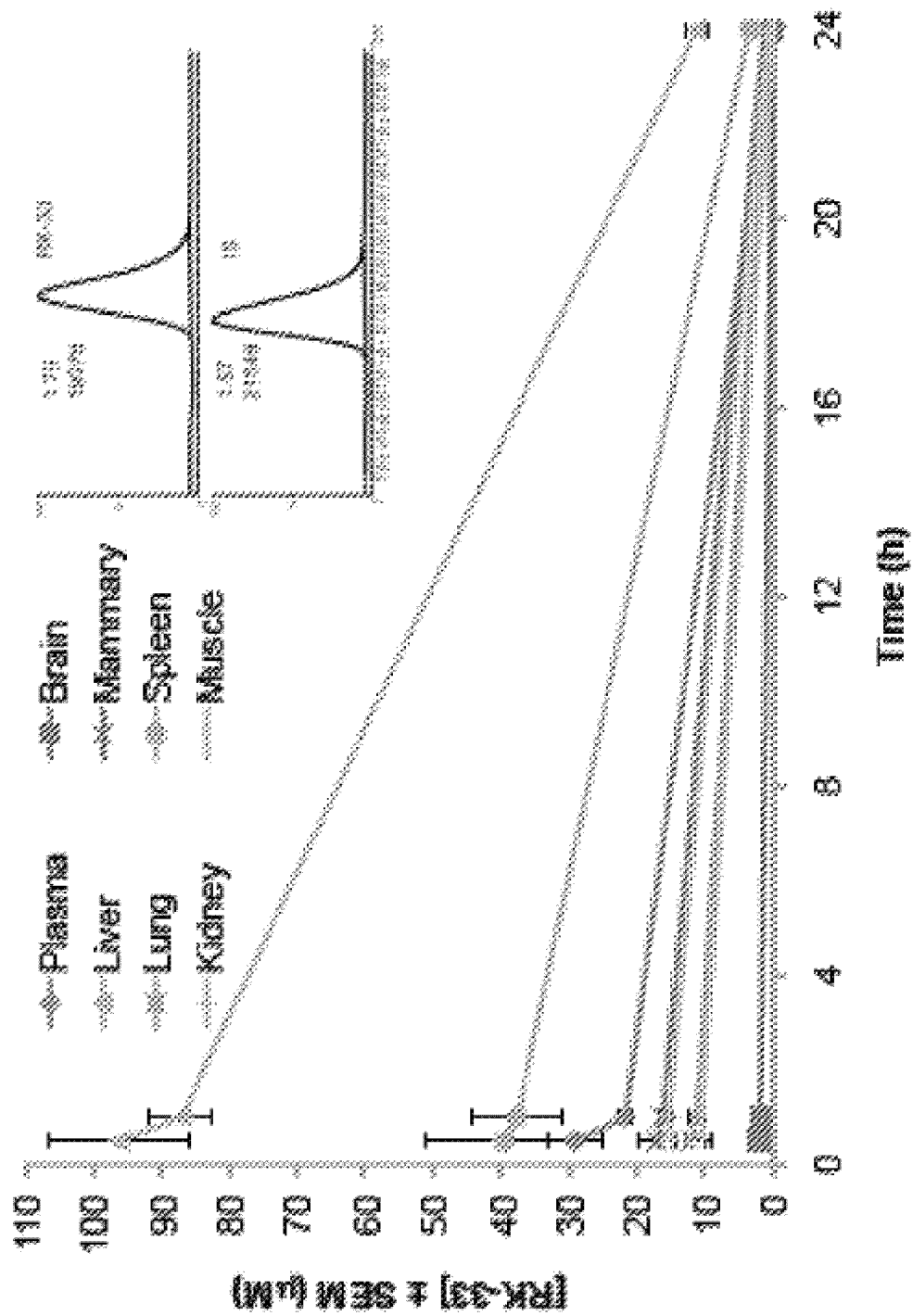

FIG. 21 illustrates MTS assays of U87 cells (glioblastoma human cell line) incubated with Compound 3 of the invention;

FIG. 22 illustrates MTS assays of PC3 cells (prostate cancer cell line) incubated with Compound 3 of the invention;

FIG. 23 illustrates photomicrographs of normal tissue sections and prostate carcinoma tissue sections stained with DDX3 antibody;

FIG. 24 illustrates photomicrographs of chondrosarcoma and pleomorphic sarcoma tissue sections stained with DDX3 antibody;

FIG. 25 shows exemplary photomicrographs of normal brain tissue, glioblastoma and medulloblastoma;

FIG. 26 illustrates immunoblot analyses for DDX-3 expression in lung, prostate, and glioblastoma cell lines;

FIGS. 27-31 illustrate Toxicity studies of Compound 3 in SCID mouse. Data shown is for control and untreated samples of brain (cerebellum) (FIG. 27), kidney (FIG. 28), Liver (FIG. 29), spleen (FIG. 30), and blood (FIG. 31); and FIG. 32 is a set of curves illustrating the biodistribution of Compound 3 in mice at different time intervals using an LC/MS/MS method. A total of five mice per time point were used for this study.

DETAILED DESCRIPTION OF THE INVENTION

Definitions

As used herein and unless otherwise indicated, the term "alkoxy group" means an —O-alkyl group, wherein alkyl is as defined herein. An alkoxy group can be unsubstituted or substituted with one or two suitable substituents. Preferably, the alkyl chain of an alkyloxy group is from 1 to 6 carbon atoms in length, referred to herein, for example, as "($C_1$-$C_{10}$) alkoxy."

As used herein and unless otherwise indicated, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein and unless otherwise indicated, the term "alkylalkoxy" or "alkyloxyalkyl group" means a saturated, monovalent unbranched or branched hydrocarbon chain covalently bonded to an oxygen and covalently bonded to a second a saturated, monovalent unbranched or branched hydrocarbon chain (e.g., -alkyl-O-alkyl).

As used herein and unless otherwise indicated, the term "alkyl" or "alkyl group" means a substituted or unsubstituted, saturated, monovalent unbranched or branched hydrocarbon chain. Examples of alkyl groups include, but are not limited to, ($C_1$-$C_{10}$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein and unless otherwise indicated, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "($C_6$)aryl."

As used herein and unless otherwise indicated, the term "aryloxy group" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "($C_6$)aryloxy."

As used herein, the term "benzyl" means —$CH_2$-phenyl.

As used herein, the term "carbonyl" group is a divalent group of the formula —C(O)—.

As used herein and unless otherwise indicated, the term "compounds of the invention" means, collectively, the compounds of formulas I, II, III, IV, and V and pharmaceutically acceptable salts thereof as well as compounds depicted herein including Compounds 3, 11, 12, 13, 14, 21, 23, 25, 27, and 101-193. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein and unless otherwise indicated, the term "cylclic alkyl" and "cycloalkyl group" are used synonymously and each means a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the term "formulation" refers to a composition comprising a compound of the invention that is described in a particular dosage form (e.g., tablet) or with a particular dosage amount (e.g., 30 mg/kg).

As used herein and unless otherwise indicated, the term "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phienyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$ heteroaryl."

As used herein and unless otherwise indicated, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 7 carbon atoms and form 1 to 3 heteroatoms, referred to herein as $(C_1-C_7)$heterocycloalkyl.

As used herein and unless otherwise indicated, the term "heterocyclic radical" or "heterocyclic ring" means a heterocycloalkyl group or a heteroaryl group.

As used herein and unless otherwise indicated, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. Preferably, the hydrocarbon chain of a hydrocarbyl group is from 1 to 6 carbon atoms in length, referred to herein as "$(C_1-C_6)$hydrocarbyl."

When administered to a subject (e.g., to an animal for veterinary use or to a human for clinical use), the compounds of the invention can be optionally administered in isolated form. As used herein, "isolated" means that the compounds of the invention are separated from other components of either (a) a natural source, such as a plant or cell, preferably bacterial culture, or (b) a synthetic organic chemical reaction mixture, preferably, via conventional techniques, the compounds of the invention are purified. As used herein, "purified" means that when isolated, the isolate contains at least 80% preferably at least 90%, more preferably at least 95%, and most preferably at least 99% of a compound of the invention by weight of the isolate.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxy-ethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, a amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "phenyl" means —$C_6H_5$. A phenyl group can be unsubstituted or substituted with one or two suitable substituents.

As used herein and unless otherwise indicated, the terms "substituted" and "a suitable substituent" means a group that does not nullify the synthetic or pharmaceutical utility of the compounds of the invention or the intermediates useful for preparing them. Examples of substituted groups or suitable substituents include, but are not limited to: ($C_1$-$C_8$)alkyl; ($C_1$-$C_8$)alkenyl; ($C_1$-$C_8$)alkynyl; ($C_6$)aryl; ($C_3$-$C_5$)heteroaryl; ($C_3$-$C_7$)cycloalkyl; ($C_1$-$C_8$)alkoxy; ($C_6$)aryloxy; —CN; —OH; SH, oxo; halo, —$NO_2$, —$CO_2H$; —$NH_2$; —NHOH, —NH(($C_1$-$C_8$)alkyl); —N(($C_1$-$C_8$)alkyl)$_2$; —NH(($C_6$)aryl); —NHO(($C_1$-$C_8$)alkyl); —N(O($C_1$-$C_8$)alkyl)$_2$; —NH(O($C_6$)aryl); —S(($C_1$-$C_8$)alkyl); —S(($C_1$-$C_8$)alkyl)$_2$; —S(($C_6$)aryl); (=O); C(S), —N(($C_6$)aryl)$_2$; —CHO; —C(O)(($C_1$-$C_8$)alkyl); —C(O)(($C_6$)aryl); —$CO_2$(($C_1$-$C_8$)alkyl); and —$CO_2$(($C_6$)aryl), —C(S)(($C_1$-$C_8$)alkyl); —C(S)(($C_6$)aryl); —$SO_2$(($C_1$-$C_8$)alkyl); —$SO_2$(($C_6$)aryl), and —$SO_3H$, —C(S)O(($C_1$-$C_8$)alkyl); —C(S)(O)(($C_6$)aryl). In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl. One of skill in art can readily choose a suitable substituent based on the stability and pharmacological and synthetic activity of the compound of the invention.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated.

The terms "treating or preventing" are intended to include preventing, eradicating, or inhibiting the resulting increase of undesired physiological activity associated with a disorder, for example, in the context of the therapeutic or prophylactic methods of the invention. In another embodiment, the term treating or preventing includes antagonistic effects, e.g., diminishment of the activity or production of mediators of a disorder.

As used herein, the term "proliferative disease", "hyperproliferative disorder", "disease caused by uncontrolled cell growth" and the like includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a preneoplastic lesion, carcinoma in situ, oral hairy leukoplakia, or psoriasis. Cancer and tumors are particular examples of proliferative disease. In accordance with one or more embodiments, the term cancer can include, for example cancers of the lung, liver, pancreas, prostate, breast, kidney, and central nervous system including the brain (for example, glioblastoma, medulloblastoma, and pontine tumors), related tumors. In accordance with one or more embodiments, the cancers treated by the present invention include cancers which are resistant to hypoxia, or chemotherapy, such as, for example, tamoxifen or taxol resistant cancers.

Exemplary Compounds Useful for Practicing the Invention

As set forth herein, the compounds useful in practicing the invention include, but are not limited to, compounds as described in Formula I-V set forth herein, as well as specific compounds disclosed elsewhere in this specification, and compositions and formulations containing those compounds or a pharmaceutically acceptable salt or prodrug thereof. These compounds are useful for treatment and identification methods of the invention, for example for treating, preventing or identifying a disease or disorder susceptible to treatment by downregulation of DDX3 expression including, but not limited to, conditions caused by uncontrolled cell growth, hyperproliferation of cells, tumor growth, and cancers, for example, pancreatic cancer, liver cancer, breast cancer, lung cancer, prostate cancer, brain cancer including glioblastoma, medulloblastoma, and pontine tumors, kidney cancer, leukemia, or a sarcoma, which comprises administering to a mammal in need of such treatment or prevention a therapeutically or prophylactically effective amount of a composition comprising a compound of Formula I-V, or a pharmaceutically acceptable salt or prodrug thereof, and a pharmaceutically acceptable vehicle. In certain embodiments, a composition or formulation comprising a compound of Formula I-V is useful in treating or preventing conditions caused by uncontrolled cell growth. In certain embodiments, a composition or formulation comprising a compound of Formula I-V is useful in killing abnormal or cancerous cells while simultaneously not affecting healthy or normal cells. In certain embodiments, a composition or formulation comprising a compound of Formula I-V act as cytotoxic agents. In certain embodiments, a composition or formulation comprising a compound of Formula I-V act as apoptotic agents.

The invention encompasses methods of treating or preventing diseases and disorders described herein by administering a composition or formulation comprising a compound of Formulas I-V or a pharmaceutically acceptable salt or prodrug thereof.

As described herein, the compositions that are useful in the methods of the invention encompass compounds of Formulas I-V.

In one embodiment, the invention encompasses compounds and compositions and formulations for treating or preventing diseases or disorders comprising a compound of Formula (I):

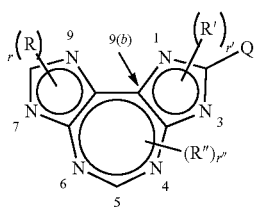

or pharmaceutically acceptable salts and prodrugs thereof, wherein:

R, R', and R" are each independently a hydrogen, hydroxyl; substituted or unsubstituted: cyclic or acyclic alkyl group, cyclic or acyclic alkenyl group, cyclic or acyclic alkynyl group, aryl group, alkylaryl group, arylalkyl group, benzyl group, cyclic and acyclic heteroalkyl group, heteroaryl group; —C(O)R$^3$; —C(S)R$^3$; —S(O)R$^3$; —S(O)$_2$R$^3$; —C(O)NR$^3$R$^4$; —C(S)NR$^3$R$^4$; —C(S)YR$^3$; —C(O)YR$^3$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;

R, R', and R" can also form a ring with one or more C, S, O, N atoms such that, for example, R and R' together include:

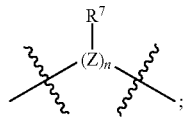

R$^7$ is a hydrogen; hydroxyl; substituted and unsubstituted: cyclic and acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)NR$^3$R$^4$; —C(S)alkyl; —C(S)alkenyl; —C(S)alkynyl; —C(S)aryl; —C(S)benzyl; —C(S)NR$^3$R$^4$; —C(O)NR$^3$R$^4$; —C(S)YR$^3$; —C(O)YR$^3$;

wherein
----- Q is =O, =NH, or =S;
Y is O or S;
Z is CH, N, P, or C;
----- is a single bond or double bond; wherein if ----- is a double bond, R$^2$ or R$^7$ is independently O, S, or NH;
n is 1, 2, 3, or 4;
R$^3$ and R$^4$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and
r, r', and r" are each independently an integer from 1 to 3.

In certain illustrative embodiments, R, R', and R" are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In certain illustrative embodiments, the compounds of the invention do not include compounds where both R, R', and R" are all hydrogen.

In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In one embodiment, R is hydrogen. In another embodiment, R is an alkyl group. In another embodiment, R is an alkoxy group. In another embodiment, R is an alkylalkoxy group. In another embodiment, R is an alkenyl group. In another embodiment, R is alkynyl group. In another embodiment, R is an aryl group. In another embodiment, R is aryloxy group. In another embodiment, R is benzyl group. In another embodiment, R is heteroaryl group. In another embodiment, R is heterocycloalkyl group. In another embodiment, R is a cycloalkyl group. In another embodiment, R is a benzyl group.

In certain illustrative embodiments, R is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, and triazolyl.

In one embodiment, R' is hydrogen. In another embodiment, R' is an alkyl group. In another embodiment, R' is an alkoxy group. In another embodiment, R' is an alkylalkoxy group. In another embodiment, R' is an alkenyl group. In another embodiment, R' is alkynyl group. In another embodiment, R' is an aryl group. In another embodiment, R' is aryloxy group. In another embodiment, R' is benzyl group. In another embodiment, R' is heteroaryl group. In another embodiment, R' is heterocycloalkyl group. In another embodiment, R' is a cycloalkyl group. In another embodiment, R' is a benzyl group.

In certain illustrative embodiments, R' is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl.

In another embodiment, R" is hydrogen. In another embodiment, R" is an alkyl group. In another embodiment, R" is an alkoxy group. In another embodiment, R" is an alkylalkoxy group. In another embodiment, R" is an alkenyl group. In another embodiment, R" is alkynyl group. In another embodiment, R" is an aryl group. In another embodiment, R" is aryloxy group. In another embodiment, R" is benzyl group. In another embodiment, R" is heteroaryl group. In another embodiment, R" is heterocycloalkyl group. In another embodiment, R" is a cycloalkyl group. In another embodiment, R" is a benzyl group.

In certain illustrative embodiments, R" is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl.

In another embodiment, the invention encompasses compositions and formulations for treating or preventing diseases or disorders comprising a compound of Formula (II):

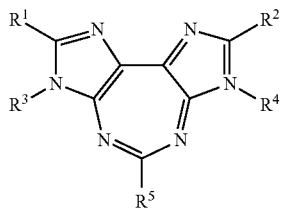

(II)

or pharmaceutically acceptable salts and prodrugs thereof, wherein $R^1$, $R^2$, $R^3$, $R^4$, and $R^5$ are each independently a hydrogen; hydroxyl; substituted or unsubstituted: cyclic or acyclic alkyl group, cyclic or acyclic alkenyl group, cyclic or acyclic alkynyl group, aryl group, alkylaryl group, arylalkyl group, benzyl group, cyclic or acyclic heteroalkyl group, heteroaryl group; —C(O)$R^6$; —C(S)$R^6$; —S(O)$R^6$; —S(O)$_2R^6$; —C(O)N$R^6R^8$; —C(S)N$R^6R^8$; C(S)Y$R^6$; —C(O)Y$R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;

$R^1$ and $R^3$ or $R^2$ and $R^4$ can also form a ring with one or more C, S, O, N atoms such that $R^1$ and $R^3$ or $R^2$ and $R^4$ together include

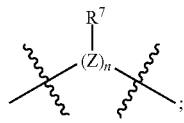

$R^7$ is a hydrogen; hydroxyl; substituted and unsubstituted: cyclic or acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)N$R^6R^8$; —C(S)alkyl; —C(S)alkenyl; —C(S)alkynyl; —C(S)aryl; —C(S)benzyl; —C(S)N$R^6R^8$; —C(O)Y$R^6$; or —C(S)Y$R^6$ wherein Y is O or S;

Z is CH, N, P, or C;

----- is a single bond or double bond; wherein if ----- is a double bond, $R^2$ or $R^7$ is independently O, S, or NH;

$R^6$ and $R^8$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and n is 1, 2, 3, or 4.

In certain illustrative embodiments, $R^1$, $R^2$, $R^3$, $R^4$, and $R^5$ are each independently a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In one embodiment, $R^1$ is hydrogen. In another embodiment, $R^1$ is an alkyl group. In another embodiment, $R^1$ is an alkoxy group. In another embodiment, $R^1$ is an alkylalkoxy group. In another embodiment, $R^1$ is an alkenyl group. In another embodiment, $R^1$ is alkynyl group. In another embodiment, $R^1$ is an aryl group. In another embodiment, $R^1$ is aryloxy group. In another embodiment, $R^1$ is benzyl group. In another embodiment, $R^1$ is heteroaryl group. In another embodiment, $R^1$ is heterocycloalkyl group. In another embodiment, $R^1$ is a cycloalkyl group. In another embodiment, $R^1$ is a benzyl group.

In certain illustrative embodiments, $R^1$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl.

In one embodiment, $R^2$ is hydrogen. In another embodiment, $R^2$ is an alkyl group. In another embodiment, $R^2$ is an alkoxy group. In another embodiment, $R^2$ is an alkylalkoxy group. In another embodiment, $R^2$ is an alkenyl group. In another embodiment, $R^2$ is alkynyl group. In another embodiment, $R^2$ is an aryl group. In another embodiment, $R^2$ is aryloxy group. In another embodiment, $R^2$ is benzyl group. In another embodiment, $R^2$ is heteroaryl group. In another embodiment, $R^2$ is heterocycloalkyl group. In another embodiment, $R^2$ is a cycloalkyl group. In another embodiment, $R^2$ is a benzyl group.

In certain illustrative embodiments, $R^2$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl.

In one embodiment, $R^3$ is hydrogen. In another embodiment, $R^3$ is an alkyl group. In another embodiment, $R^3$ is an alkoxy group. In another embodiment, $R^3$ is an alkylalkoxy group. In another embodiment, $R^3$ is an alkenyl group. In another embodiment, $R^3$ is alkynyl group. In another embodiment, $R^3$ is an aryl group. In another embodiment, $R^3$ is aryloxy group. In another embodiment, $R^3$ is benzyl group. In another embodiment, $R^3$ is heteroaryl group. In another embodiment, $R^3$ is heterocycloalkyl group. In another embodiment, $R^3$ is a cycloalkyl group. In another embodiment, $R^3$ is a benzyl group.

In certain illustrative embodiments, $R^3$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, NO$_2$, or triazolyl. In one embodiment, $R^5$ is hydrogen. In another embodiment, $R^5$ is an alkyl group. In another embodiment, $R^5$ is an alkoxy group. In another embodiment, $R^5$ is an alkylalkoxy group. In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a benzyl group substituted with one or groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In another embodiment, the invention encompasses compositions and formulations for treating or preventing diseases or disorders comprising a compound of Formula (III):

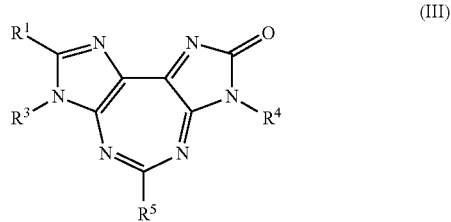

(III)

or pharmaceutically acceptable salts and prodrugs thereof, wherein
$R^1$, $R^3$, $R^4$, and $R^5$ are each independently a hydrogen; hydroxyl; substituted or unsubstituted: cyclic or acyclic alkyl group, cyclic or acyclic alkenyl group, cyclic or acyclic alkynyl group, aryl group, alkylaryl group, arylalkyl group, benzyl group, cyclic and acyclic heteroalkyl group, heteroaryl group; —C(O)$R^6$; —C(S)$R^6$; —S(O)$R^6$; —S(O)$_2R^6$; —C(O)NR$^6R^7$; —C(S)NR$^6R^7$; C(S)YR$^6$; —C(O)YR$^6$; —O-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;
$R^1$ and $R^3$ can also form a ring with one or more C, S, O, N atoms such that $R^1$ and $R^3$ together include

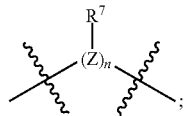

;

$R^7$ is a hydrogen; hydroxyl; substituted and unsubstituted: cyclic or acyclic alkyl group, group, alkenyl group, alkynyl group, aryl group, aryloxy group, alkylary group, aryalkyl group, heteroaryl group, heterocycloalkyl group; —C(O)alkyl; —C(O)alkenyl; —C(O)alkynyl; —C(O)aryl; —C(O)benzyl; —C(O)NR$^3R^4$; —C(S)alkyl; —C(S)alkenyl; —C(S)alkynyl; —C(S)aryl; —C(S)benzyl; —C(S)NR$^3R^4$; —C(O)NR$^3R^4$; —C(S)YR$^3$; —C(O)YR$^3$;
wherein
Y is O or S;
Z is CH, N, P, or C;
----- is a single bond or double bond; wherein if ----- is a double bond, $R^2$ or $R^7$ is independently O, S, or NH;
$R^6$ and $R^8$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and
n is 1, 2, 3, or 4.

In certain illustrative embodiments, $R^1$, $R^3$, $R^4$, and $R^5$ are not all hydrogen.

In certain illustrative embodiments, $R^1$, $R^3$, $R^4$, and $R^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

In one embodiment, $R^1$ is hydrogen. In another embodiment, $R^1$ is an alkyl group. In another embodiment, $R^1$ is an alkoxy group. In another embodiment, $R^1$ is an alkylalkoxy group. In another embodiment, $R^1$ is an alkenyl group. In another embodiment, R is alkynyl group. In another embodiment, $R^1$ is an aryl group. In another embodiment, R is aryloxy group. In another embodiment, $R^1$ is benzyl group. In another embodiment, $R^1$ is heteroaryl group. In another embodiment, $R^1$ is heterocycloalkyl group. In another embodiment, $R^1$ is a cycloalkyl group. In another embodiment, $R^1$ is a benzyl group.

In certain illustrative embodiments, $R^1$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl. In one embodiment, $R^3$ is hydrogen. In another embodiment, $R^3$ is an alkyl group. In another embodiment, $R^3$ is an alkoxy group. In another embodiment, $R^3$ is an alkylalkoxy group. In another embodiment, $R^3$ is an alkenyl group. In another embodiment, $R^3$ is alkynyl group. In another embodiment, $R^3$ is an aryl group. In another embodiment, $R^3$ is aryloxy group. In another embodiment, $R^3$ is benzyl group. In another embodiment, $R^3$ is heteroaryl group. In another embodiment, $R^3$ is heterocycloalkyl group. In another embodiment, $R^3$ is a cycloalkyl group. In another embodiment, $R^3$ is a benzyl group.

In certain illustrative embodiments, $R^3$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In one embodiment, $R^5$ is hydrogen. In another embodiment, $R^5$ is an alkyl group. In another embodiment, $R^5$ is an alkoxy group. In another embodiment, $R^5$ is an alkylalkoxy group. In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In another embodiment, the invention encompasses compositions and formulations for treating or preventing diseases or disorders comprising a compound of Formula (IV):

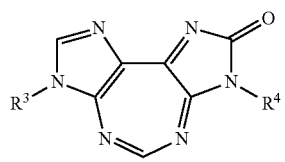

(IV)

or pharmaceutically acceptable salts and prodrugs thereof, wherein $R^3$ and $R^4$ are each independently a hydrogen; hydroxyl; substituted or unsubstituted: cyclic or acyclic alkyl group, cyclic or acyclic alkenyl group, cyclic a or nd acyclic alkynyl group, aryl group, alkylaryl group, arylalkyl group, benzyl group, cyclic or acyclic heteroalkyl group, heteroaryl group; —C(O)$R^5$; —C(S)$R^5$; —S(O)$R^5$; —S(O)$_2$ $R^5$; —C(O)NR$^5$R$^6$; —C(S)NR$^5$R$^6$; —C(O)YR$^5$; —C(S) YR$^5$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;

$R^5$ and $R^6$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and Y is O or S.

In certain illustrative embodiments, $R^3$ and $R^4$ are both not hydrogen.

In certain illustrative embodiments, $R^3$ and $R^4$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In one embodiment, $R^3$ is hydrogen. In another embodiment, $R^3$ is an alkyl group. In another embodiment, $R^3$ is an alkoxy group. In another embodiment, $R^3$ is an alkylalkoxy group. In another embodiment, $R^3$ is an alkenyl group. In another embodiment, $R^3$ is alkynyl group. In another embodiment, $R^3$ is an aryl group. In another embodiment, $R^3$ is aryloxy group. In another embodiment, $R^3$ is benzyl group. In another embodiment, $R^3$ is heteroaryl group. In another embodiment, $R^3$ is heterocycloalkyl group. In another embodiment, $R^3$ is a cycloalkyl group. In another embodiment, $R^3$ is a benzyl group.

In certain illustrative embodiments, $R^3$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In another embodiment, the invention encompasses compositions and formulations for treating or preventing diseases or disorders comprising a compound of Formula (V):

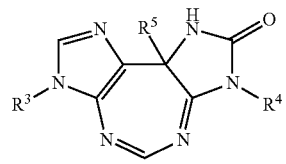

(V)

or pharmaceutically acceptable salts and prodrugs thereof, wherein $R^3$, $R^4$, and $R^5$ are each independently a hydrogen; hydroxyl; substituted or unsubstituted: cyclic or acyclic alkyl group, cyclic or acyclic alkenyl group, cyclic or acyclic alkynyl group, aryl group, alkylaryl group, arylalkyl group, benzyl group, cyclic or acyclic heteroalkyl group, heteroaryl group; —C(O)$R^6$; —C(S)$R^6$; —S(O)$R^6$; —S(O)$_2$$R^6$; —C(O)NR$^6$R$^7$; —C(S)NR$^6$R$^7$; C(S)YR$^6$; —C(O)YR$^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; or ribose or deoxyribose sugars substituted with one or more halogens;

$R^5$ and $R^6$ are independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, heteroaryl group, heterocycloalkyl group; and Y is O or S.

In certain illustrative embodiments, $R^3$, $R^4$, and $R^5$ are not each hydrogen.

In certain illustrative embodiments, $R^3$, $R^4$, and $R^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —NO$_2$, triazolyl.

In one embodiment, $R^3$ is hydrogen. In another embodiment, $R^3$ is an alkyl group. In another embodiment, $R^3$ is an alkoxy group. In another embodiment, $R^3$ is an alkylalkoxy group. In another embodiment, $R^3$ is an alkenyl group. In another embodiment, $R^3$ is alkynyl group. In another embodiment, $R^3$ is an aryl group. In another embodiment, $R^3$ is aryloxy group. In another embodiment, $R^3$ is benzyl group. In another embodiment, $R^3$ is heteroaryl group. In another embodiment, $R^3$ is heterocycloalkyl group. In another embodiment, $R^3$ is a cycloalkyl group. In another embodiment, $R^3$ is a benzyl group.

In certain illustrative embodiments, $R^3$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In one embodiment, $R^4$ is hydrogen. In another embodiment, $R^4$ is an alkyl group. In another embodiment, $R^4$ is an alkoxy group. In another embodiment, $R^4$ is an alkylalkoxy group. In another embodiment, $R^4$ is an alkenyl group. In another embodiment, $R^4$ is alkynyl group. In another embodiment, $R^4$ is an aryl group. In another embodiment, $R^4$ is aryloxy group. In another embodiment, $R^4$ is benzyl group. In another embodiment, $R^4$ is heteroaryl group. In another embodiment, $R^4$ is heterocycloalkyl group. In another embodiment, $R^4$ is a cycloalkyl group. In another embodiment, $R^4$ is a benzyl group.

In certain illustrative embodiments, $R^4$ is a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

In one embodiment, $R^5$ is hydrogen. In another embodiment, $R^5$ is an alkyl group. In another embodiment, $R^5$ is an alkoxy group. In another embodiment, $R^5$ is an alkylalkoxy group. In another embodiment, $R^5$ is an alkenyl group. In another embodiment, $R^5$ is alkynyl group. In another embodiment, $R^5$ is an aryl group. In another embodiment, $R^5$ is aryloxy group. In another embodiment, $R^5$ is benzyl group. In another embodiment, $R^5$ is heteroaryl group. In another embodiment, $R^5$ is heterocycloalkyl group. In another embodiment, $R^5$ is a cycloalkyl group. In another embodiment, $R^5$ is a benzyl group.

In certain illustrative embodiments, $R^5$ is a phenyl or a benzyl group substituted with one or more groups or atoms selected from F, Cl, Br, I, OH, azido, SH, alkyl, aryl, heteroalkyl, alkyloxyl, alkylthiol, amino, hydroxylamino, N-alkylamino, N,N-dialkylamino, N,N-dimethylamino, acyl, alkyloxycarbonyl, sulfonyl, urea, $NO_2$, or triazolyl.

Illustrative examples of compounds that are encompassed by Formulas I-V and that are useful in the methods of the invention include, but are not limited to:

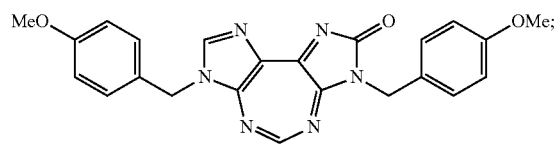

3

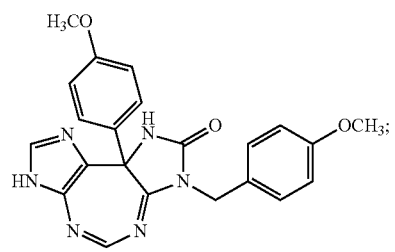

11

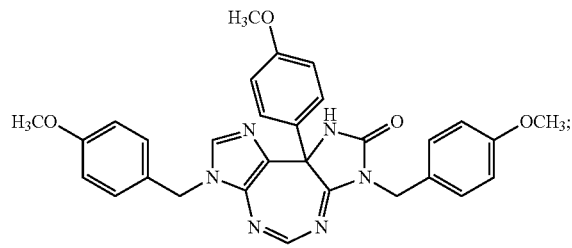

12

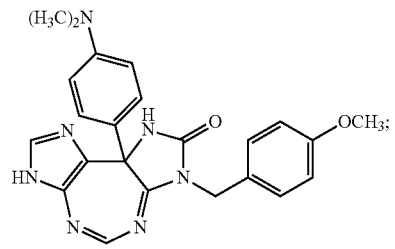

13

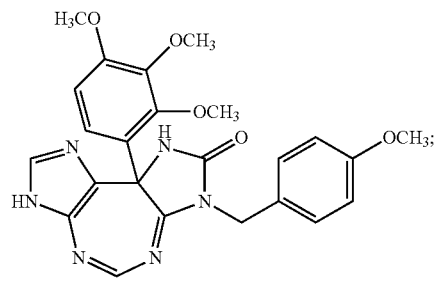

14

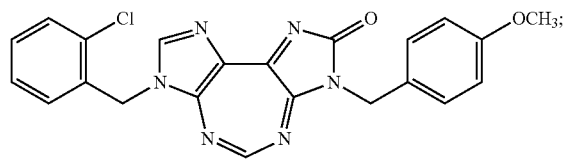

21

-continued
23
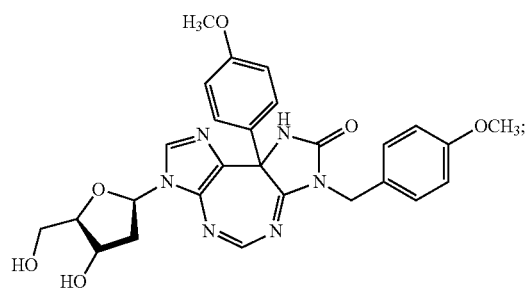
25
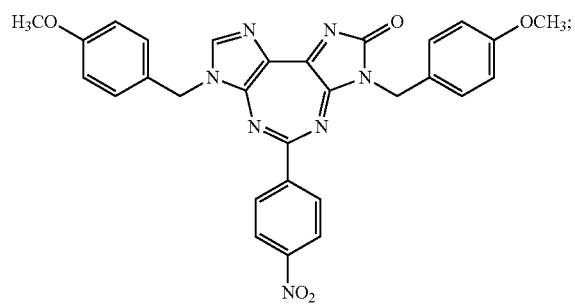
27
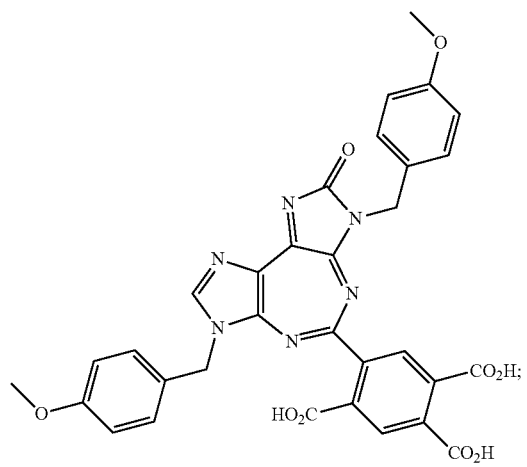
101
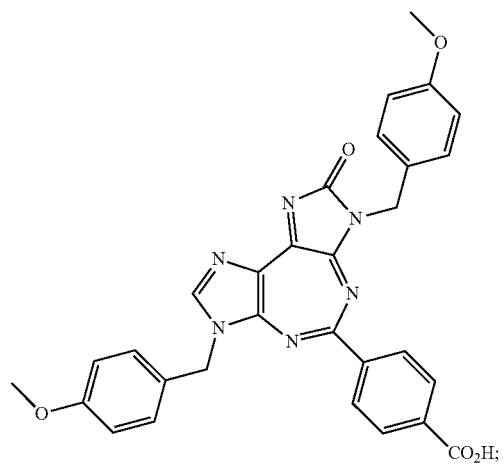
102
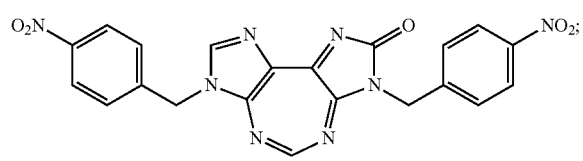
103
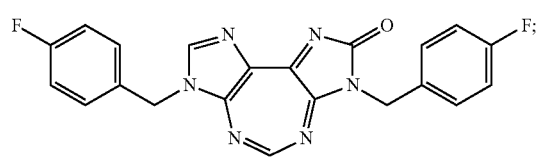
104
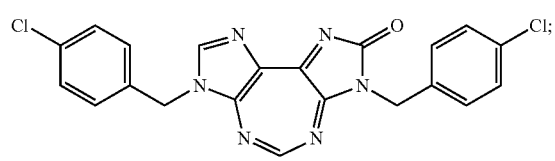
105
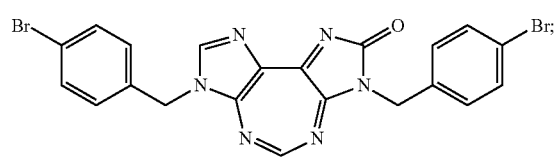
106
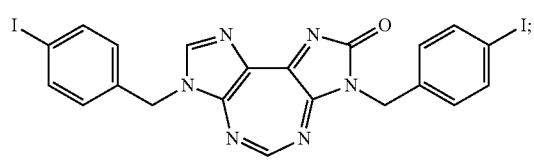
107
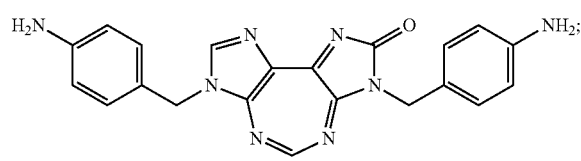
108
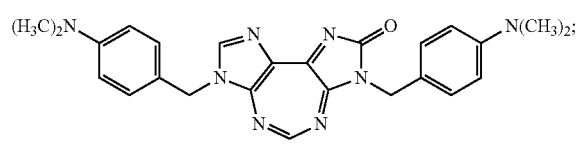
109
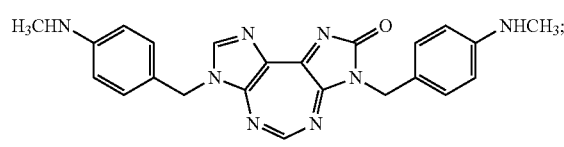

-continued
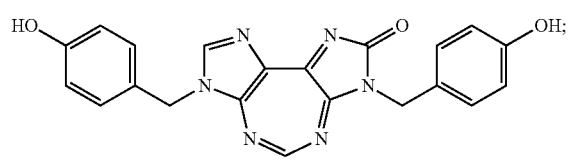
110
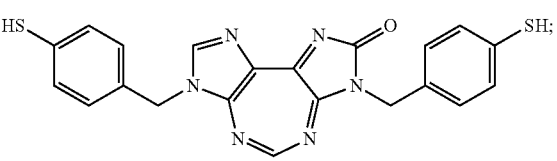
111
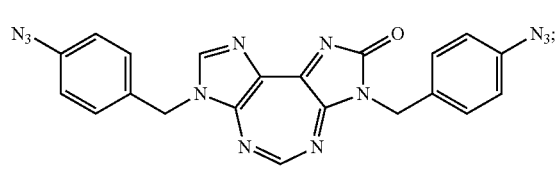
112
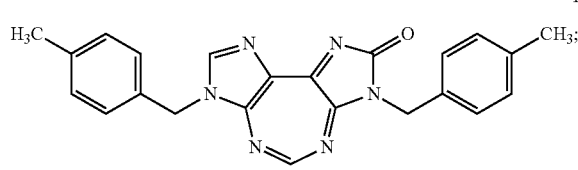
113
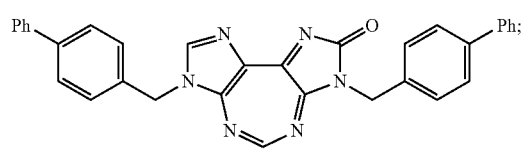
114
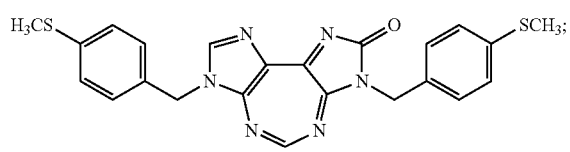
115
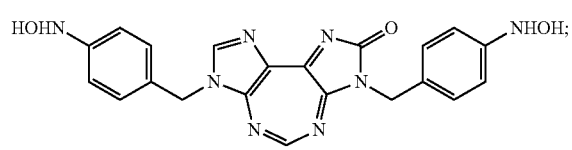
116
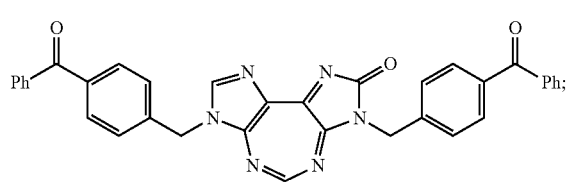
117
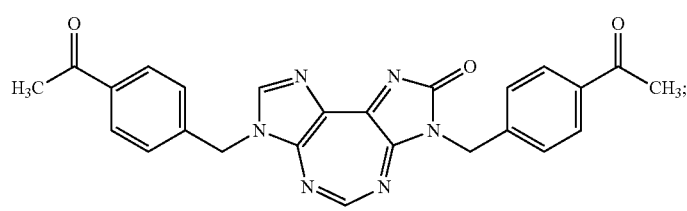
118
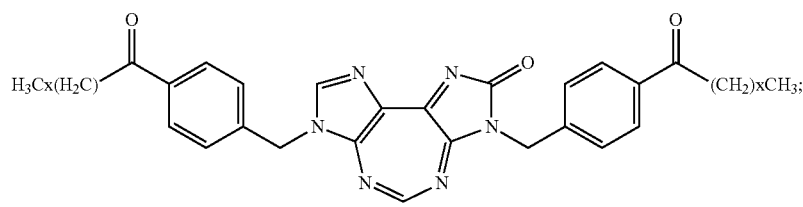
x = 1-17
119
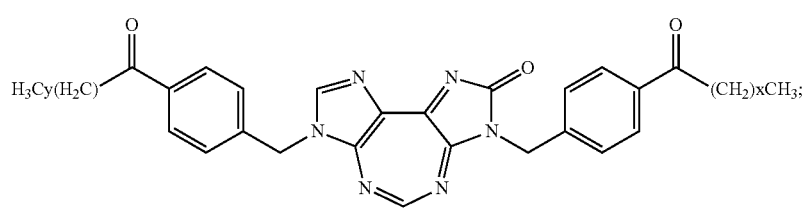
x = 1-17
y = 1-17
120

-continued
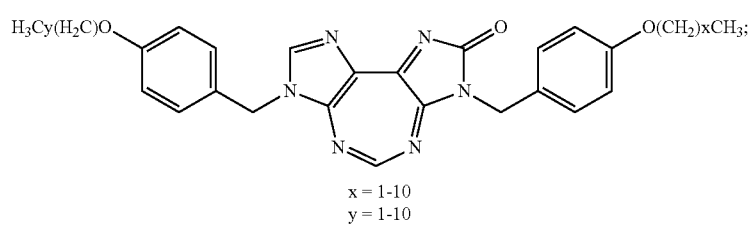
121
x = 1-10
y = 1-10
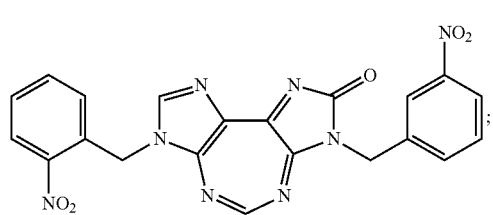
122
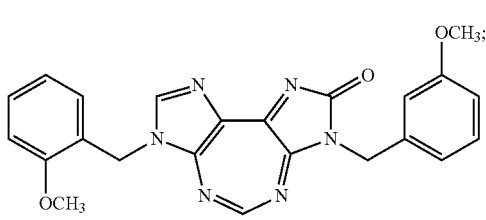
123
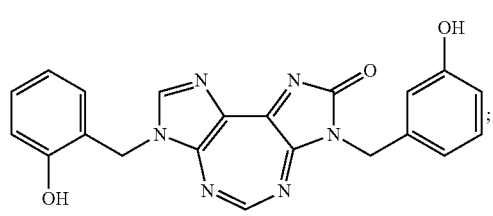
124
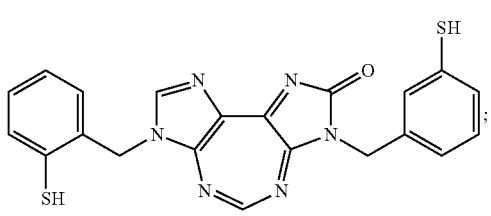
125
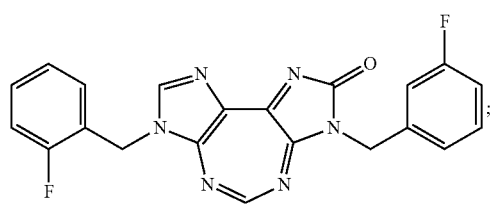
126
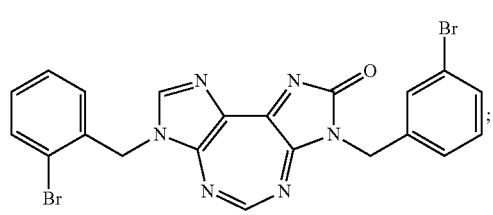
128
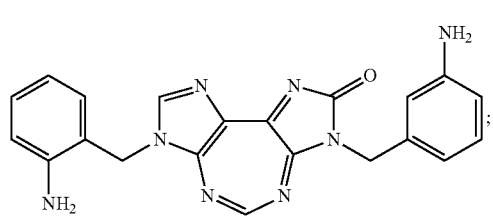
130
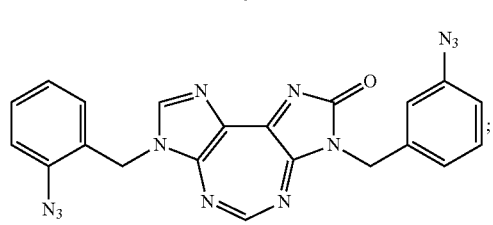
132
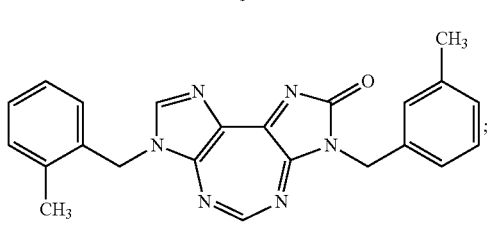
133

-continued
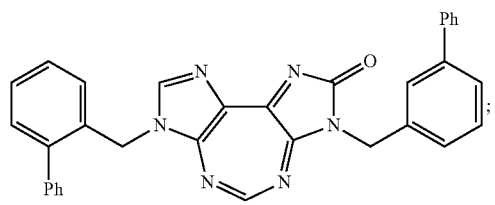
134
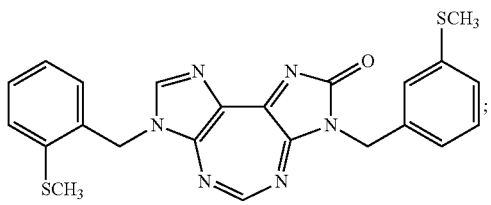
135
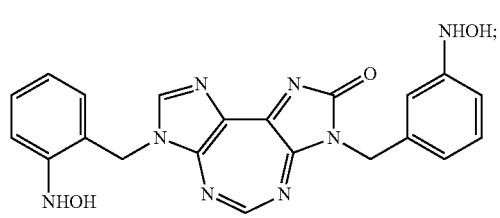
136
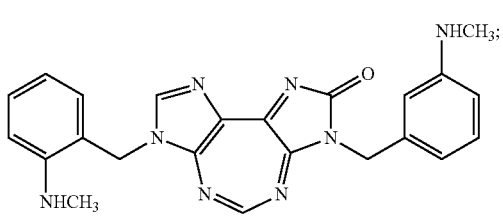
137
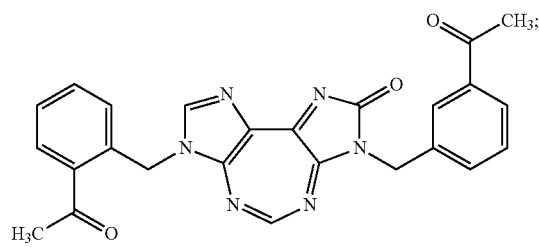
138
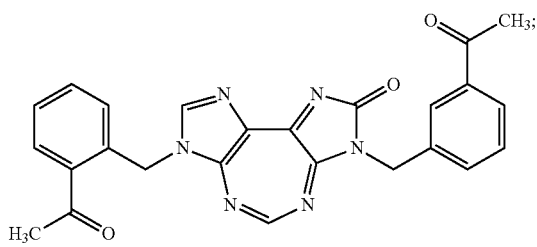
139
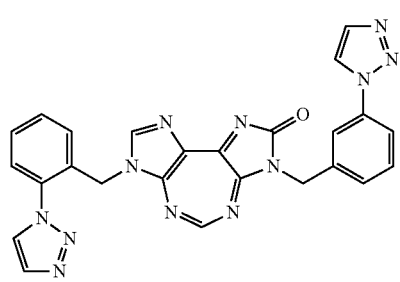
140
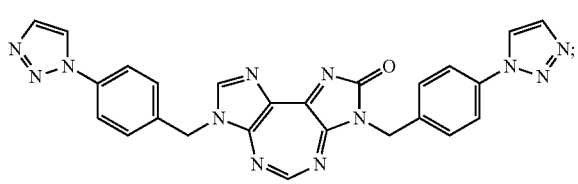
141
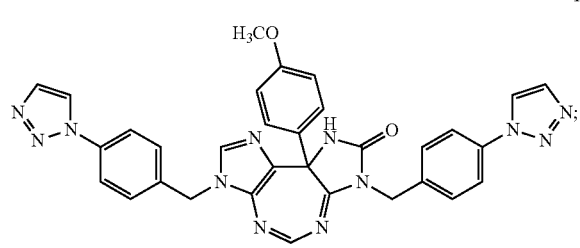
142
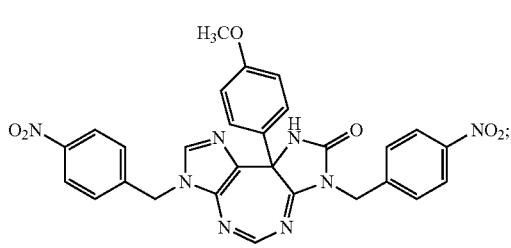
143
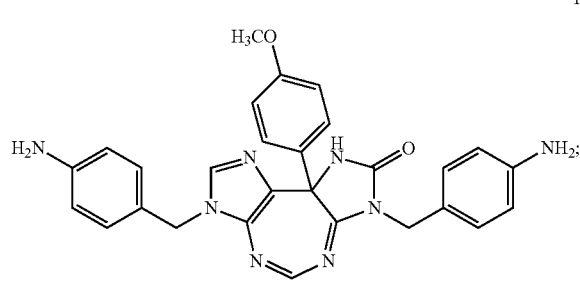
144
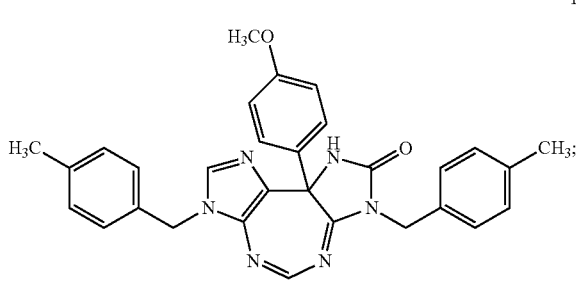
145

146
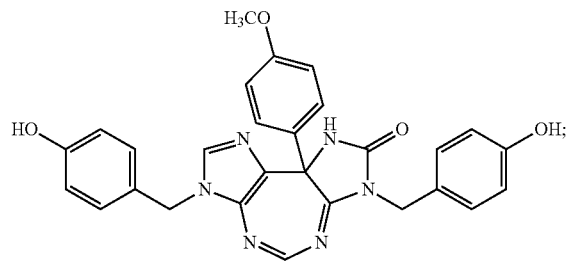
147
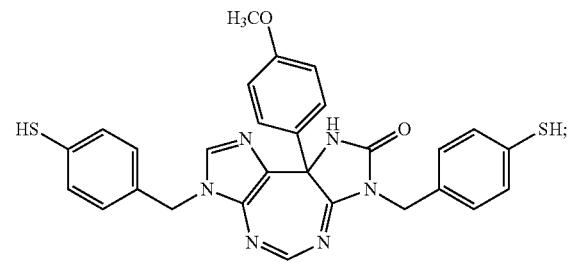
148
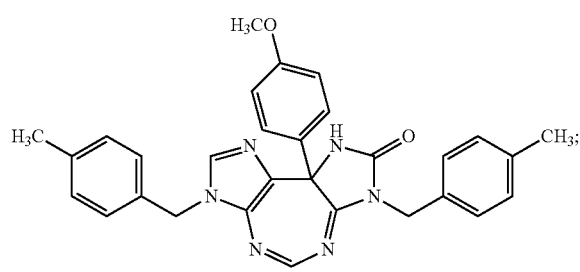
149
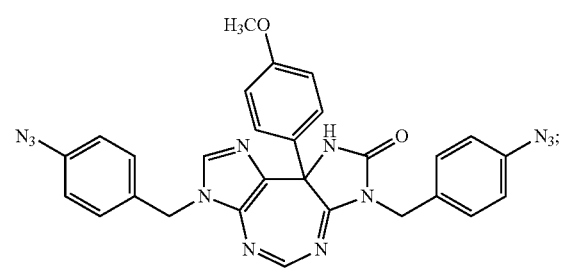
150
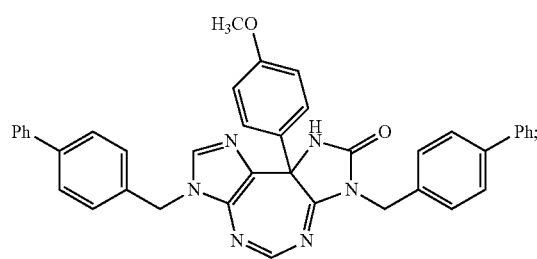
151
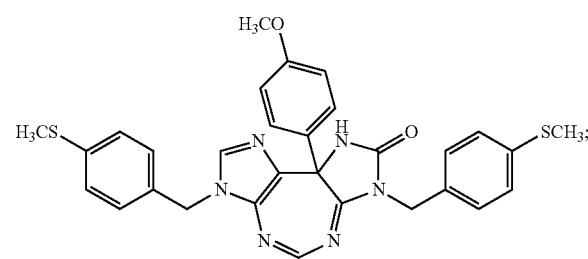
152
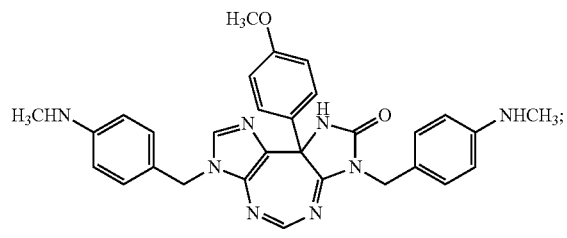
153
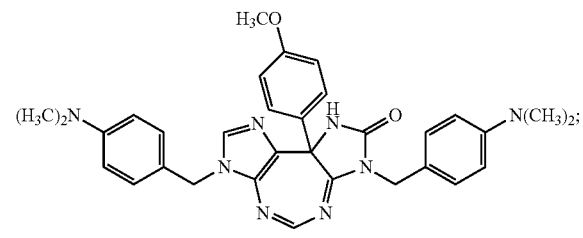
154
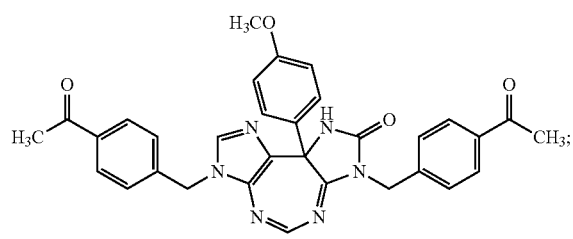
155
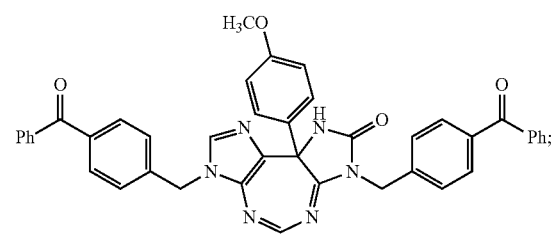
156
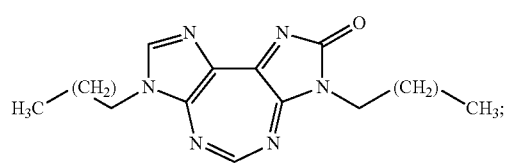
157
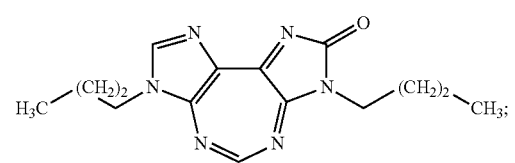

-continued
| 158 | 159 |
|---|---|
| 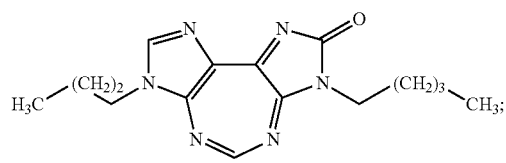 | 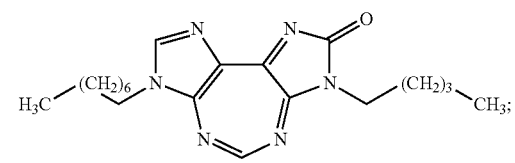 |
| 160 | 161 |
| 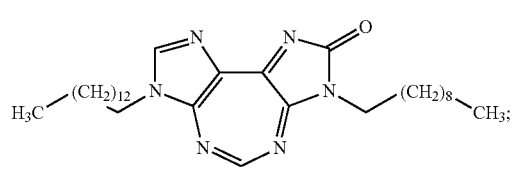 | |
| 162 | 163 |
| 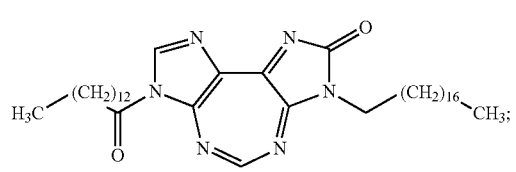 | |
| 164 | 165 |
| 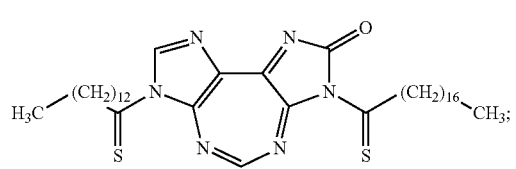 | |
| 166 | 167 |
| 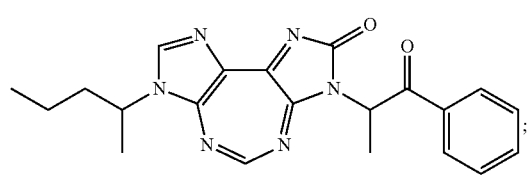 | 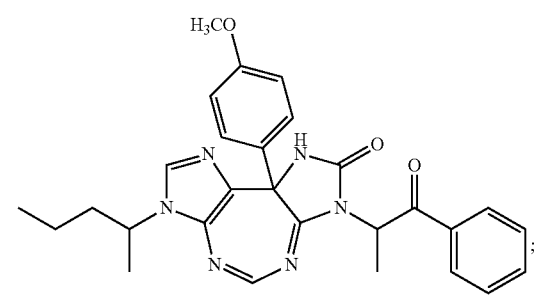 |
| 168 | 169 |
| 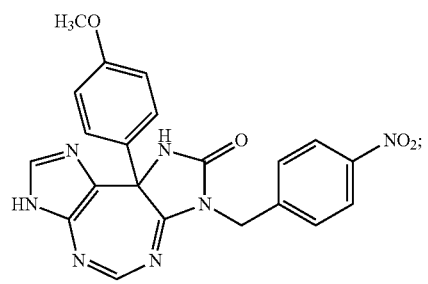 | |
| 170 | 171 |
| 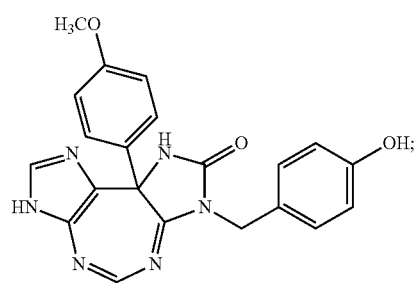 | 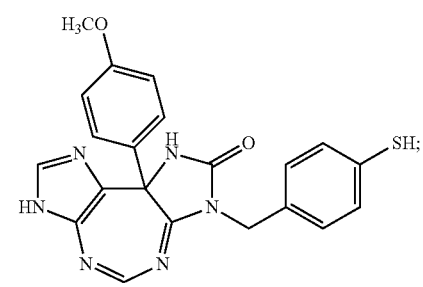 |

-continued
172
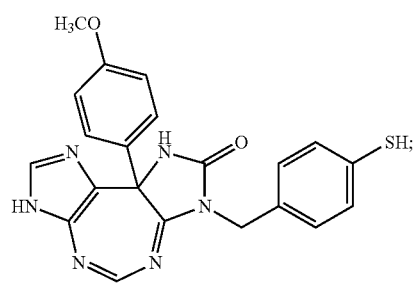
173
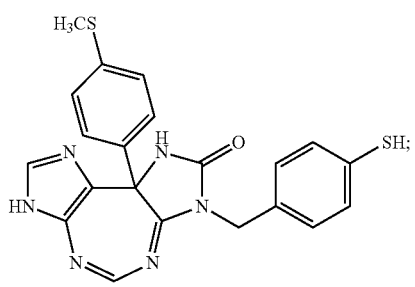
174
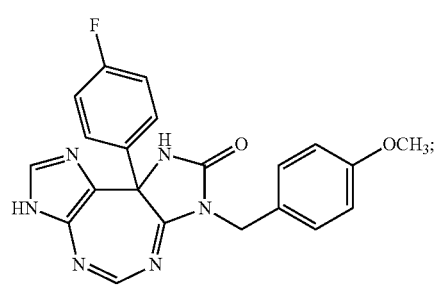
175
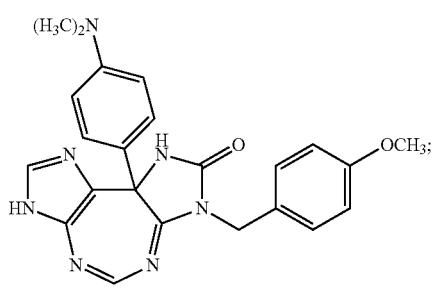
176
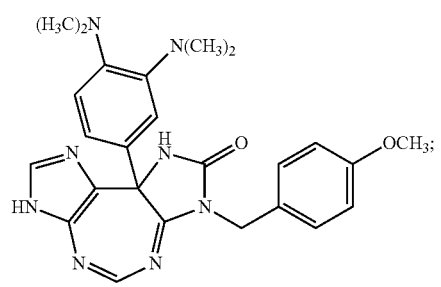
177
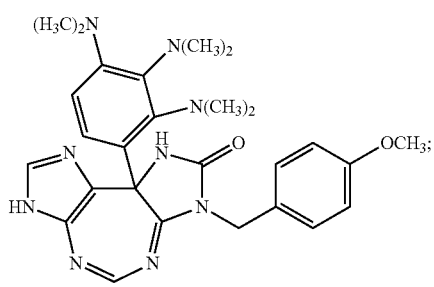
178
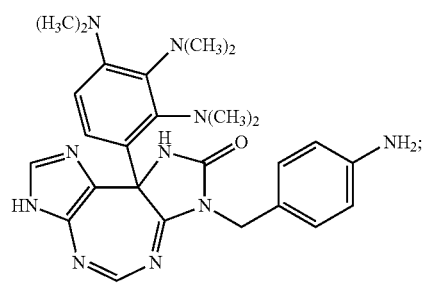
179
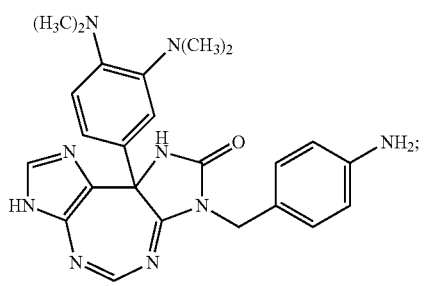
180
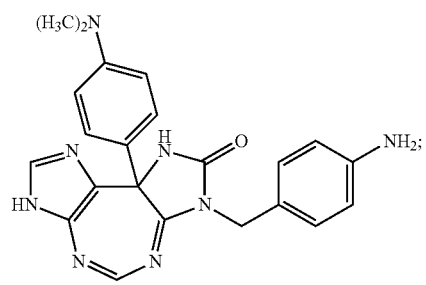
181
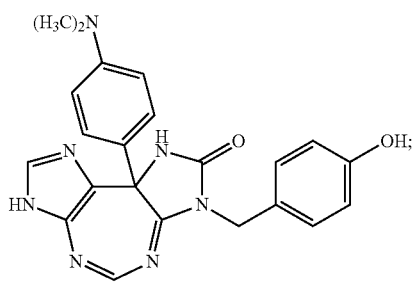

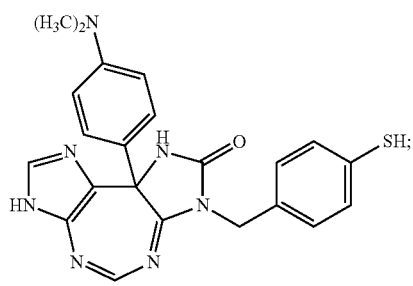
182
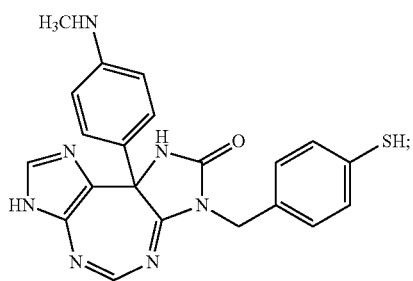
183
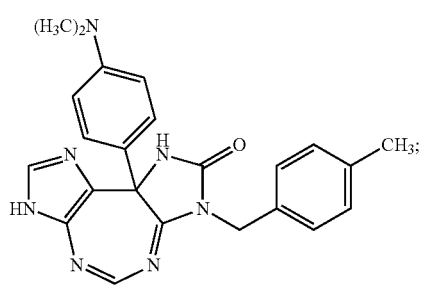
184
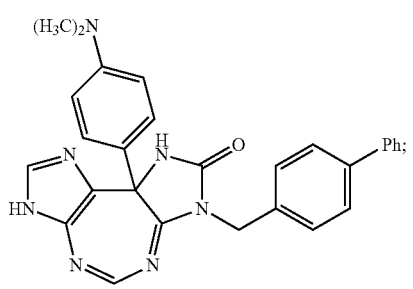
185
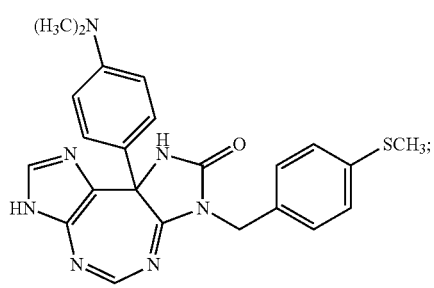
186
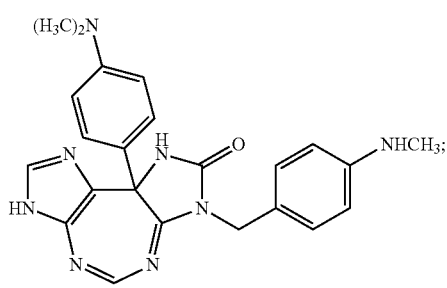
187
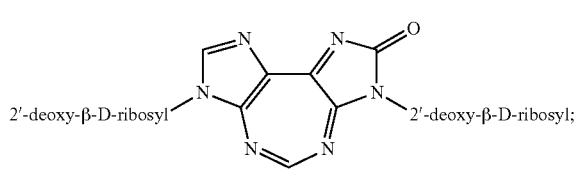
188
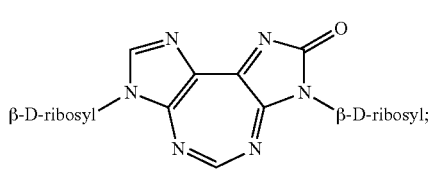
189

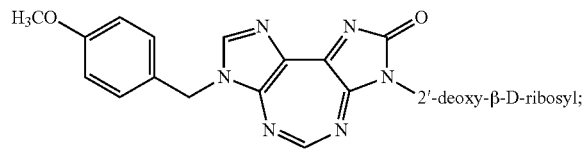

190

2'-deoxy-β-D-ribosyl;

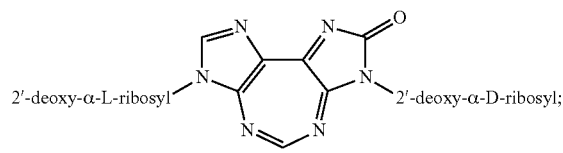

191

2'-deoxy-α-L-ribosyl;  2'-deoxy-α-D-ribosyl;

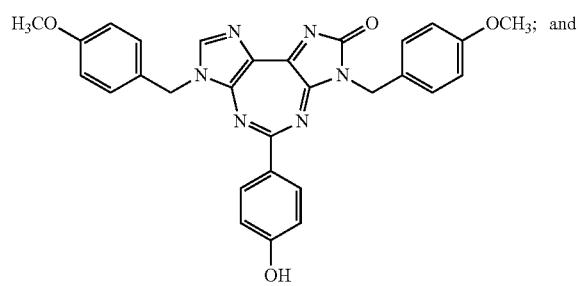

192

OCH₃; and

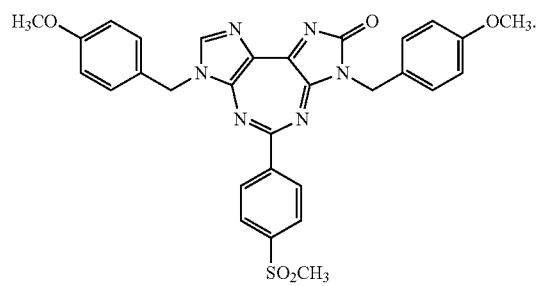

193

It will be understood that above compounds are illustrative only and not intended to limit the scope of the claims to only those compounds.

The compounds of the invention can be synthesized by organic chemistry techniques known to those of ordinary skill in the art, for example, as described in International Application No. PCT/US2009/005273. An exemplary synthesis is generally described in Scheme 1 below.

Scheme 1

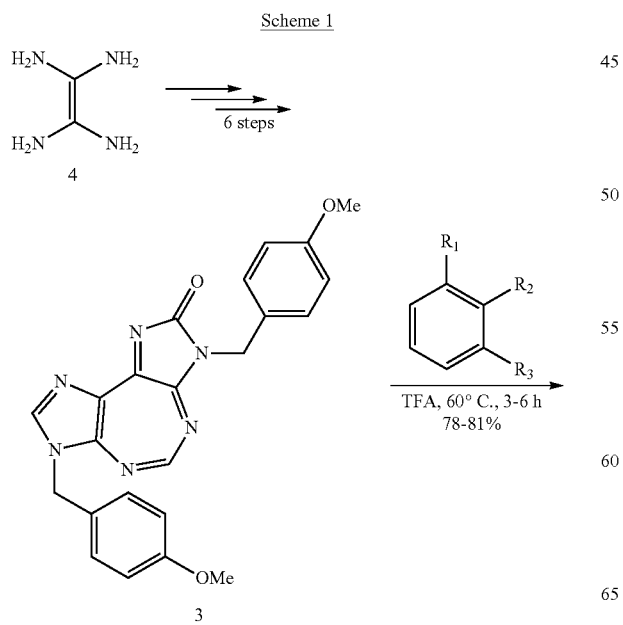

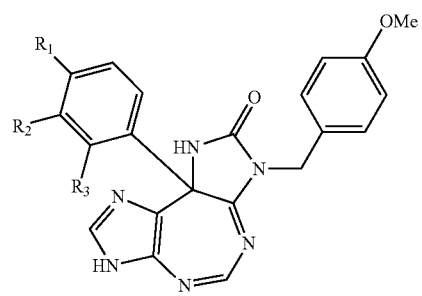

11; R₁ = OMe; R₂ = R₃ = H
13; R₁ = N(Me)₂; R₂ = R₃ = H
14; R₁ = R₂ = R₃ = OMe

The target 5:7:5 heterocyclic ring system was yet unknown. Scheme 2 illustrates the first entry into such a ring system employing an illustrative representative example 3, containing a removable p-methoxybenzyl (PMB) group attached to each of the two imidazole rings.

Scheme 2
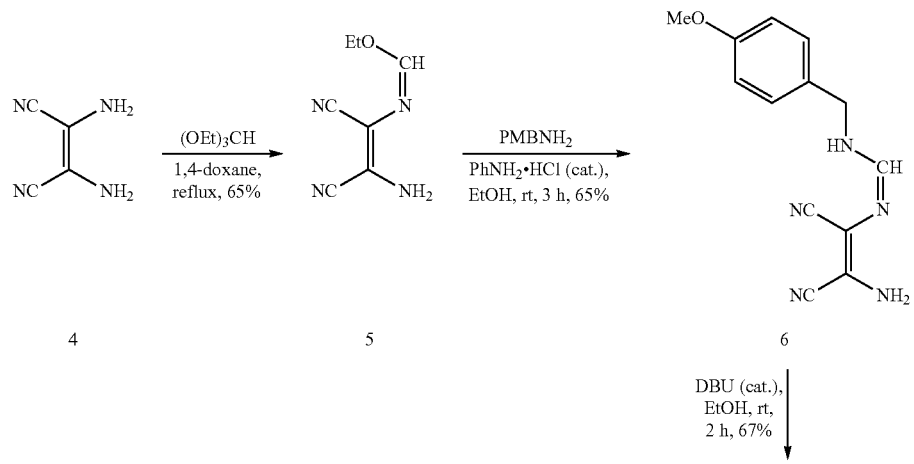
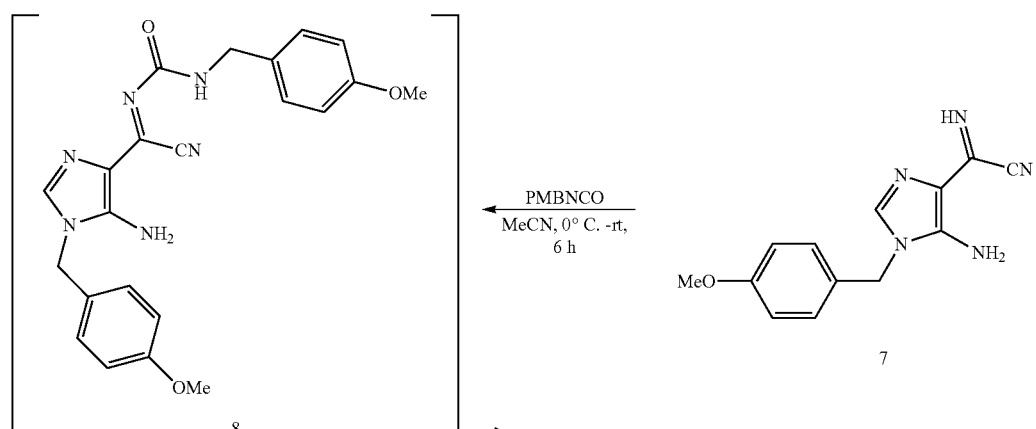
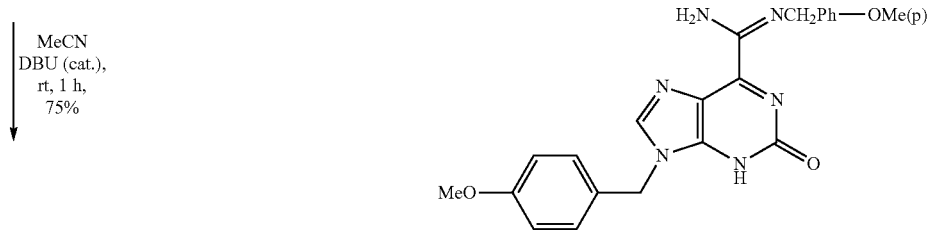

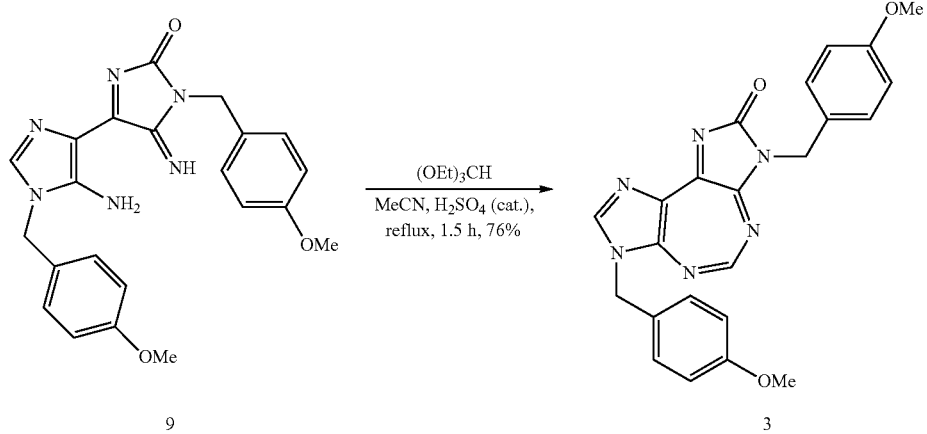

Generally, an illustrative compound of the invention can be synthesized by heating diaminomaleonitrile 4 with triethyl orthoformate in dioxane yielded formimidate 5. (See, e.g., Sun, Z.; Hosmane, R. S. *Synth. Commun.* 2001, 31, 549). The reaction of 5 with p-methoxybenzylamine catalyzed by aniline hydrochloride formed formimidine 6 (See, e.g., Yahya-Zadeh, A.; Booth, B. L. *Synth. Commun.* 2001, 31, 3225), which underwent intramolecular cyclization in the presence of DBU to form imidazole derivative 7. (See, e.g., Yahyazadeh, A.; Sharifi, Z. *Phosphorus, Sulfur, Silicon, Relat. Elem.* 2006, 181, 1339). The treatment of latter with p-methoxybenzyl isocyanate resulted into a mixture of urea 8 and 9. (See, e.g., Dias, A. M.; Cabral, I.; Proenca, M. F.; Booth, B. L. *J. Org. Chem.* 2002, 67, 5546). The complete coversion of 8 into 9 was achieved by treating the mixture with DBU in acetonitrile. (Id.). The reaction of isolated 9 with triethyl orthoformate yielded the target heterocycle 3. In certain embodiments, the reported rearrangement of a compound such as 8 into an oxopurine such as 10 was not observed. In an illustrative embodiment, a rearrangement has been limited to the use of N-tosylisocyanate, but not others. (Id.). This was further corroborated by the facile ring-closure of 9 to form 3. All intermediates and final product were fully characterized by spectroscopic and analytical data. (See Example Section).

The core tricyclic structure of Compound 3 containing 14 π electrons is aromatic by the Hückel rule. Nevertheless, with six nitrogen atoms and a conjugated carbonyl group present in the heterocyclic ring system, Compound 3 is considerably electrophilic. In order to explore this aspect a little further, Compound 3 was reacted with a few carbon and nitrogen nucleophiles. Illustrative examples of the carbon nucleophiles attempted include anisole, N,N-dimethylaniline, and 1,2,3-trimethoxybenzene, all of which contain electron-donating substituent(s) on their aromatic rings. Thus, the reaction of a mixture of 3 (1 mmol), anisole (5 mL), and TFA (10 mL) at 60° C. for 3 h (Scheme 3) formed a novel product 11 which was isolated, purified (81%) and characterised.

In order to elucidate the pathway of formation of 11 from 3, the latter (1 mmol) was treated with a mixture of TFA (10 mL) and anisole (5 mL) 16 at rt for 12 h (Scheme 4), which yielded a mixture of 11 (10%) and 12 (60%) which was found to be an adduct of anisole by spectroscopic and analytical data. Surprisingly, 12 was converted into 11 when heated with TFA at 60° C. for 1 h. This suggests that the reaction proceeds by first addition of anisole, followed by selective cleavage of the N-3 PMB group. As TFA is often used to remove the PMB group from heterocyclic rings, the observed deprotection of one of the imidazole rings under these conditions is not totally surprising. (See, e.g., Miki, Y.; Hachiken, H.; Kashima, Y.; Sugimura, W.; Yanase, N. *Heterocycles* 1998, 48, 1).

Scheme 4

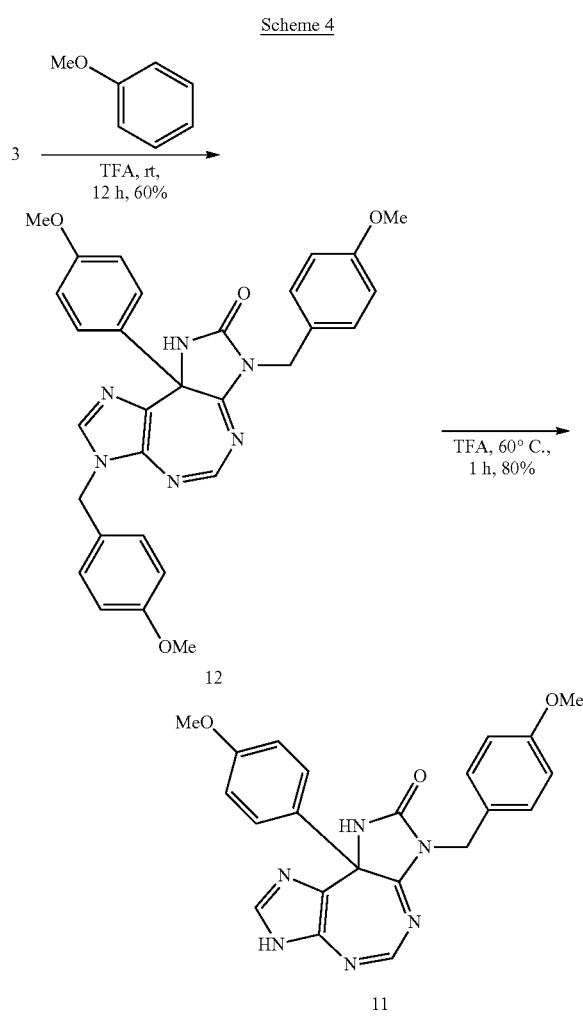

The generality of the above reaction was studied using two other electron-rich carbon nucleophiles, including N,N-dimethylaniline and 1,2,3-trimethoxybenzene. Thus, when 3 (1 mmol) was heated separately (Scheme 5) at 60° C. for 6 h with N,N-dimethylaniline (5 mL) or 1,2,3-trimethoxy benzene (5 mL) in TFA (10 mL), compound 13 (78%) or 14 (80%), was formed, respectively.

In certain illustrative embodiments, the structures of 3 and 11-14 were determined by 1D and 2D NMR experiments (some important peaks and correlations are presented in FIG. 2 with an example of 12; and Tables 1-3), including HMQC, HMBC and DEPT experiments. In the HMBC spectra, H-5 showed the correlations with C-6a and C-11; H-1' showed correlation with C-8, C-3' and C-7'; C-8 showed correlations with H-1'. The addition of anisole/1,2,3-trimethoxybenzene/ N,N-dimethylaniline at position 9a was determined by the correlation of H-2"(or/and) and H-6" with C-9a; two-bond coupling enhancement between C-9a and H-9 (N) and H-9 (N) and C-8.

Expression of DDX3

DDX3 is overexpressed in a number of different types of cancers. However, normal tissue does not typically express DDX3. It has been shown that cell viability in cell lines is reduced upon treatment with compounds that downregulate DDX3 or downregulate DDX3 expression. Significantly, as a result of this differential expression, compounds that target DDX3, such as those disclosed herein and in particular Compound 3, show lower toxicity to normal cells than typical chemotherapeutic agents. Specifically, cancer cell lines with high expression of DDX3 were shown to be responsive to Compound 3. Thus, the presence of tumor cells that express DDX3 can provide particularly useful treatment options, which is indicative for DDX3 to be a predictive biomarker.

The differential expression of DDX3 also provides for a biomarker that can have prognostic value with respect to detection of cancerous cells that could lead to a disease state. That is, if a tissue sample, for example a sample from a subject, is found to include cells that express DDX3, this makes it likely that those cells within the tissue could lead to a disease sate even if the disease itself is not yet detected. It was also found that the expression of DDX3 is proportional to cancer severity. More aggressive forms of cancer, for example more aggressive forms of breast cancer, have been shown by immunohistochemistry and by qRT-PCR to express DDX3 at levels higher than found in less aggressive cell types. Similarly, it has been found that as cancer severity increases, the expression of DDX3 also increases. This has also been shown by immunohistochemistry (IHC) and by qRT-PCR. The same results have been found in sample tissues. The differential expression of DDX3 thus provides for a biomarker that can have prognostic value with respect to progression of a disease state. Thus, assessment of the degree of or changes in the degree of expression of DDX3 can be an indicator of cancer severity or progress.

Scheme 5

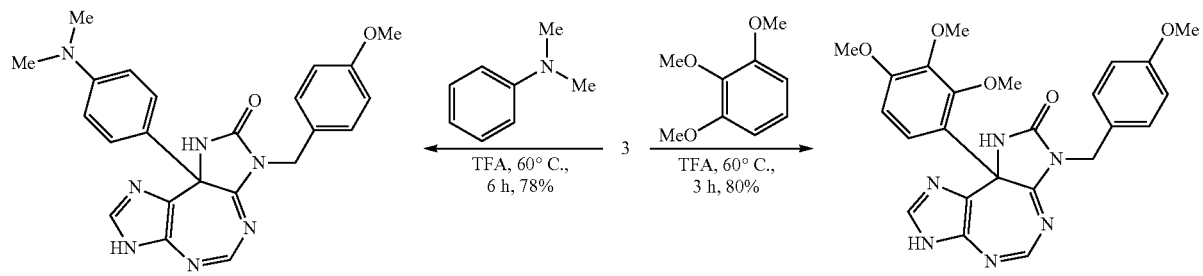

In accordance with the invention, DDX3 expression as measured by, for example, IHC or qRT-PCR analysis of tissues, can provide both a prognostic and a predictive role in cancer therapy. The observed expression of DDX3 in various cancers and its utility is described below and in the non-limiting examples that follow.

Breast Cancer

DDX3 expression was investigated by IHC in breast cancer tissue of 540 patients. Clinicopathological characteristics like age, tumor size, lymph node involvement, BRCA1 mutation status, tumor type and grade, mitotic activity index (MAI) and expression of ERα, PR, HER2, Ki-67, cyclin A, cyclin D1, p21, p27, p53, FANCD2 and EGFR were correlated with DDX3 expression and prognostic value was tested.

High cytoplasmic DDX3 expression was observed in 31% of breast cancer samples which was associated with a ductal phenotype (p=0.000), high grade (p=0.007), HER2 positive (p=0.001) and high MAI (p=0.004). Higher expression of DDX3 was observed in metastatic disease and the HER2-driven breast cancer subtype. Nuclear expression of DDX3 was shown in 12% of samples and had a negative correlation with intensity of cytoplasmic DDX3 expression (R=−0.183 p=0.012). The 5-year survival rate was 87.4% in low cytoplasmic DDX3 expressing tumors compared to 78.9% in tumors with high DDX3 expression (p=0.042).

Cytoplasmic overexpression of DDX3 in human breast cancer is associated with a more aggressive phenotype, indicating an oncogenic role for DDX3 in breast cancer. DDX3 expression could not only be used as a prognostic marker in breast cancer but could also be an excellent biomarker for treatment aimed to abrogate DDX3 function.

Lung Cancer

Lung cancer is the most common cancer worldwide, more importantly, only about 30% of non-small-cell lung cancer (NSCLC) patients respond to current combination therapy. DDX3 expression levels of 95 lung cancer patients was assessed. All lung tumor samples showed elevated levels of DDX3 but no DDX3 expression was observed in normal lung tissue. Of all lung cancer patients, 53% had high expression of DDX3 and in advanced lung cancer as much as 67% of patients had high expression of DDX3.

Accordingly, high cytoplasmic expression of DDX3 is correlated with an aggressive phenotype of lung cancer. Moreover, all lung tumors had elevated levels of DDX3. This indicates a predictive role of DDX3 expression, assessed by IHC, in the treatment allocation of lung cancer with DDX3 inhibitors.

Brain Cancers

Several different types of brain cancer have been independently assessed for DDX3 expression as described below:

Medulloblastoma is the most common malignant brain tumor of childhood. About 24% of tumors have high DDX3 expression based on IHC of 289 medulloblastoma tumors, from both pediatric and adult patients. Especially in the WNT sub group of medulloblastoma, either the DDX3X gene is mutated or DDX3 is overexpressed in about an equal amount of instances.

Pontine carcinoma is a rare form of childhood brain cancer. Nonetheless, mortality is a 100% and treatment is warranted. We have assessed 50 pontine tumors of which some showed a different expression pattern of DDX3. Although analysis of this data is still in progress these findings could lead to specific anti-DDX3 treatment in selected pontine tumor patients, based on their IHC staining pattern of DDX3.

Glioblastoma is the most common form of adult brain cancer with an abysmal morbidity and mortality and very limited treatment options. We assessed DDX3 expression In 211 glioblastoma patients, 56% had high expression of DDX3 indicating that DDX3 expression is a viable biomarker for glioblastoma.

Prostate Cancer

Prostate cancer is the most common cancer in man. DDX3 expression was evaluated in 71 prostate cancer samples. A strong correlation was observed between DDX3 and cell proliferation biomarker Ki-67 (R=0.332; p<0.001), which has been shown to be significantly associated with survival in prostate cancer (Bettencourt et al., 1996). Also, there is a trend in higher levels of DDX3 in tumors which were Gleason grade 7 or higher (OR=2.133). This is in line with previous data, which shows a significant lower survival in breast cancer patients with high expression of DDX3 (survival rate in low DDX3 expression=87.4% vs. 78.9% in high DDX3 expressing patients; p=0.042). This indicates a potential role for DDX3 in the pathogenesis of human prostate cancer. As in breast cancer, DDX3 expression could be a prognostic as well as a predictive biomarker.

Kidney Cancer

In 140 kidney tumor samples and 140 matched normal kidney samples assessed for DDX3 expression, there was an increased expression of DDX3 by IHC compared to normal tissue. Further analyses of clinicopathological features are in progress. Based on the increased expression of DDX3 in kidney tumors, DDX3 is a predictive marker for anti-DDX3 treatment in kidney cancer.

Sarcoma

A total of 158 sarcoma samples (15 subtypes—chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS) were analyzed for DDX3 expression by IHC. There was an increased expression of DDX3 by IHC in about 97% of cancer samples as compared to normal tissue. Only 5 samples (3%) had no DDX3 expression. Eighty-six samples (54%) had moderate to strong expression, and 67 samples (42%) had weak expression. These data support a role for DDX3 in sarcoma biogenesis and show that DDX3 expression could be used as a predictive biomarker for treatment with compounds that downregulate DDX3 expression such as Compound 3. Further analyses of clinicopathological features are in progress. Based on the increased expression of DDX3 in sarcomas, DDX3 is a predictive marker for anti-DDX3 treatment in sarcomas.

Therapeutic Uses of the Compounds of the Invention

In accordance with the invention, a composition or formulation comprising a compound that downregulates expression of DDX3 and optionally a pharmaceutically acceptable vehicle, is administered to a subject, particularly a mammal, for example a human, experiencing one or more of the following disorders: conditions caused by uncontrolled cell growth, hyperproliferation of cells, tumor growth, and cancers. In some embodiments, the cancer is breast cancer; lung cancer; prostate cancer; brain cancer including glioblastoma, medulloblastoma, and pontine tumors; kidney cancer; leukemia; or a sarcoma. Sarcomas include chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS). In embodiments, the disorder is one which has been previously identified as expressing DDX3 and thus susceptible to treatment by down regulation of DDX3. In some embodiments, the cancer is lung cancer. In some embodiments, the cancer is breast cancer. In some embodiments, the cancer is prostate cancer. In some embodiments, the cancer is glioblastoma In accordance with the invention, a composition or formulation comprising a fused diimidazodiazepine ring compound of the invention and optionally a pharmaceutically acceptable vehicle, is administered to a mammal, preferably a human, experiencing one or more of the following disorders: conditions caused by uncontrolled cell growth, hyperproliferation of cells, tumor growth, and cancers.

The invention also encompasses methods for treating breast cancer; lung cancer; prostate cancer; brain cancer including glioblastoma, medulloblastoma, and pontine tumors; kidney cancer; leukemia; or a sarcoma, which comprises administering to a mammal in need of such treatment or prevention a therapeutically or prophylactically effective amount of a composition comprising a compound that downregulates DDX3, or a pharmaceutically acceptable salt or prodrug thereof, and a pharmaceutically acceptable vehicle.

The invention also encompasses methods for treating or preventing breast cancer; lung cancer; prostate cancer; brain cancer including glioblastoma, medulloblastoma, and pontine tumors; kidney cancer; leukemia; or a sarcoma, which comprises administering to a mammal in need of such treatment or prevention a therapeutically or prophylactically effective amount of a composition comprising a fused diimidazodiazepine ring compound of Formula I-V, or a pharmaceutically acceptable salt or prodrug thereof, and a pharmaceutically acceptable vehicle.

In certain embodiments, a composition or formulation comprising a compound of Formula I-V is useful in treating or preventing conditions caused by uncontrolled cell growth.

In certain embodiments, a composition or formulation comprising a compound of Formula I-V is useful in killing abnormal or cancerous cells while simultaneously not affecting healthy or normal cells.

In certain embodiments, a composition or formulation comprising a compound of Formula I-V acts as a cytotoxic agent.

In certain embodiments, a composition or formulation comprising a compound of Formula I-V acts as apoptotic agent.

In one embodiment, "treatment" or "treating" and the like refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, preferably a human, as a preventative measure against such diseases. As used herein, "prevention" or "preventing" refers to a reduction of the risk of acquiring a given disease or disorder. In a preferred mode, the compositions of the present invention are administered as a preventative measure to a patient.

Therapeutic/Prophylactic Administration of Compositions and Formulations

Due to the activity of the compounds that downregulate DDX3 expression, for example the fused diimidazodiazepine ring compounds of the invention, such compounds are advantageously useful in veterinary and human medicine. As described above, these compounds of the invention are useful for the treatment or prevention of conditions caused by uncontrolled cell growth, hyperproliferation of cells, tumor growth, and cancers, for example, breast cancer; lung cancer; prostate cancer; brain cancer including glioblastoma, medulloblastoma, and pontine tumors; kidney cancer; leukemia; or a sarcoma. Include chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS). In embodiments, compounds that downregulate DDX3 expression are useful for the treatment or prevention of conditions caused by uncontrolled cell growth, hyperproliferation of cells, tumor growth, and cancers, for example, lung cancer, pancreatic cancer, leukemia, breast cancer, liver cancer, kidney cancer, human glioblastoma and prostate cancer.

The invention provides methods of treatment and prophylaxis by administering to a subject a therapeutically effective amount of a composition that includes a compound that downregulates DDX3 expression, for example a fused diimidazodiazepine ring compound as disclosed herein. The patient is a mammal, including, but not limited, to an animal such a cow, horse, sheep, pig, chicken, cat, dog, mouse, rat, rabbit, guinea pig, and is more preferably a human.

The present compositions, which comprise one or more compounds of the invention, are preferably administered intravenously or orally.

However, suitable dosage ranges of the compounds of the invention are generally about 0.0001 milligram to 2000 milligrams of a compound of the invention per kilogram body weight. In specific preferred embodiments of the invention, the oral dose is about 0.001 milligram to about 1500 milligrams per kilogram body weight, more preferably about 0.01 milligram to about 1000 milligrams per kilogram body weight, more preferably about 0.1 milligram to about 500 milligrams per kilogram body weight, and yet more preferably about 1 milligram to about 100 milligrams per kilogram body weight.

The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by A. R. Gennaro.

In another embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

It is preferred that the compositions of the invention be administered orally. Formulations for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of a compound of the invention per kilogram body weight. In specific preferred embodiments of the invention, the oral dose is about 0.01 milligram to about 100 milligrams per kilogram body weight, more preferably about 0.1 milligram to about 50 milligrams per kilogram body weight, more preferably about 0.5 milligram to about 20 milligrams per kilogram body weight, and yet more preferably about 1 milligram to about 10 milligrams per kilogram body weight. In a most preferred embodiment, the oral dose is about 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

In other embodiments, a composition of the invention for oral administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

Suitable dosage ranges for parenteral, for example, intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

In other embodiments, a composition of the invention for parenteral, for example, intravenous administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for treating depression, MS, incontinence, or IBS. The compounds of the invention may also be demonstrated to be effective and safe using animal model systems.

Other methods will be known to the skilled artisan and are within the scope of the invention.

EXAMPLES

It has been surprisingly found that downregulation of DDX3, as demonstrated, for example, by compounds described herein, can kill cancer cells but not affect normal cells at the concentration of the drug used. It has also been found that DDX3 expression is increased in certain cancers as disease states that can identify disease states and abnormal cells that can be treated by administering a compound that downregulates DDX3 expression.

Immunohistochemistry was performed as follows: Sections of 4 μm were cut, transferred on SuperFrost slides (Menzel&Glaeser, Brunswick, Germany), deparaffinized and rehydrated. Endogenous peroxidase was then blocked for 15 min with a buffer solution containing 0.3% hydrogen peroxide. Antigens were retrieved by boiling for 20 min in 10 mM citrate buffer (pH 6.0), cooled and washed with PBS. Tissue microarrays (TMAs) were incubated in a humidified chamber for 1 hour with polyclonal rabbit anti-DDX3 antibody diluted 1:1000 in PBS/1% BSA/NaN3. Subsequently, sections were washed in PBS and incubated for 30 min with secondary antibodies (Brightvision, Immunologic, Duiven, The Netherlands), washed with PBS and developed with diaminobenzidine. Slides were counterstained with hematoxylin, dehydrated and cover-slipped.

The invention is illustrated by the following non-limiting examples.

Example 1

Figure 1:
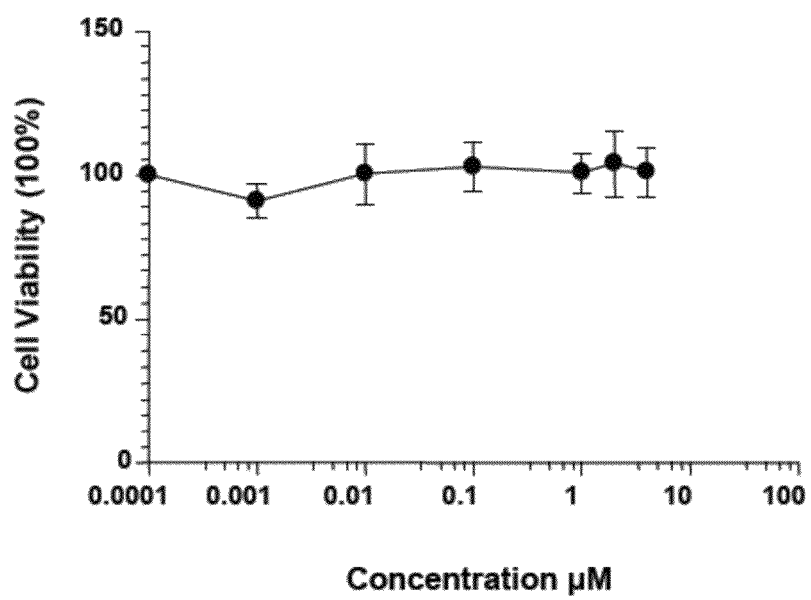
FIG. 1 illustrates the viability of normal lung cell lines when contacted with illustrative compound of the invention.
Figure 2A:
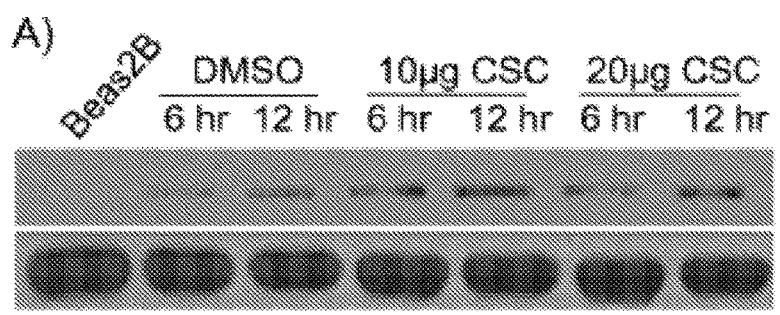
FIG. 2 shows immunoblots depicting DDX3 expression in lung cancer cell lines. 2A) DDX3 expression in Beas2B cells exposed to two different concentrations of cigarette smoke condensate (CSC).
FIG. 2B) DDX3 expression in non-small cell lung cancer cell lines (H23 and A549). Actin was used as a loading control.
Figure 2B:
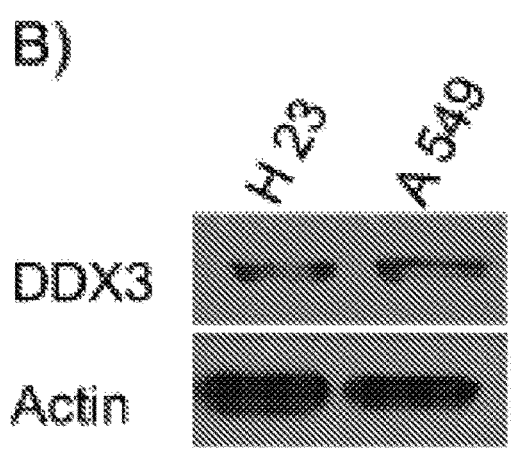
Figure 3:
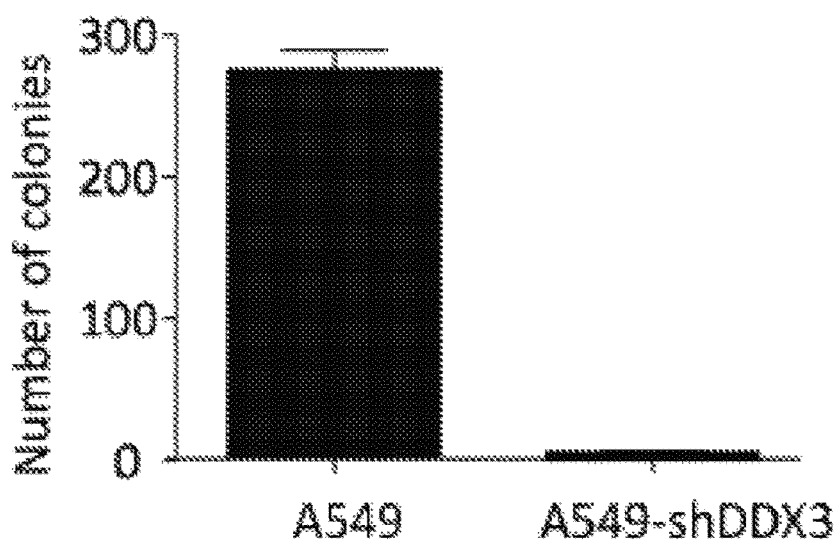
FIG. 3 is a bar graph of the number of colonies formed in soft agar assays using A549 and A549-shDDX3 cells. Experiments were done in triplicate.

The experiments show activation of DDX3 in lung cell lines (FIG. 2A). Moreover, aggressive lung cancer cell lines such as A549 and H23 exhibited robust expression of DDX3 (FIG. 2B). Importantly, down-regulation of DDX3 in A549 abrogated the colony forming abilities in soft agar assays (FIG. 3). Taken together these data indicate that DDX3 is one of the components necessary for lung cancer biogenesis and provides a novel target for lung cancer treatment.

Example 2

Figure 4:
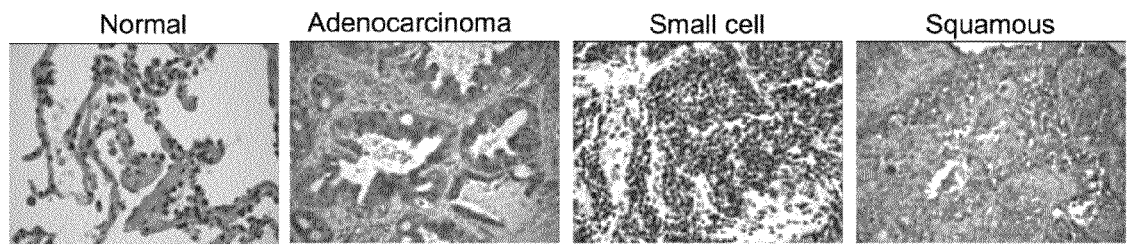
FIG. 4 is a set of photomicrographs depicting expression of DDX3 in normal lung and in different pathological stages of lung cancer.

DDX3 expression in lung cancer clinical samples. DEAD box helicases have been identified as transcriptional co-activators of both growth promoting and tumor suppressor genes. Thus, we extended our studies to evaluate the expression profile of DDX3 in lung cancer patient samples by immunohistochemistry. As shown in the photomicrographs of FIG. 4, lung adenocarcinoma sample as well as small cell carcinoma and squamous cell carcinoma showed robust DDX3 expression as compared to the normal lung. Normal lung photomicrographs were taken at 40× magnification and the lung cancer samples at 20×. Interestingly small cell carcinoma and squamous cell carcinoma had more nuclear staining than the adenocarcinoma sample. This indicates a role for DDX3 in the pathogenesis of human lung cancer.

Example 3

Figure 5:
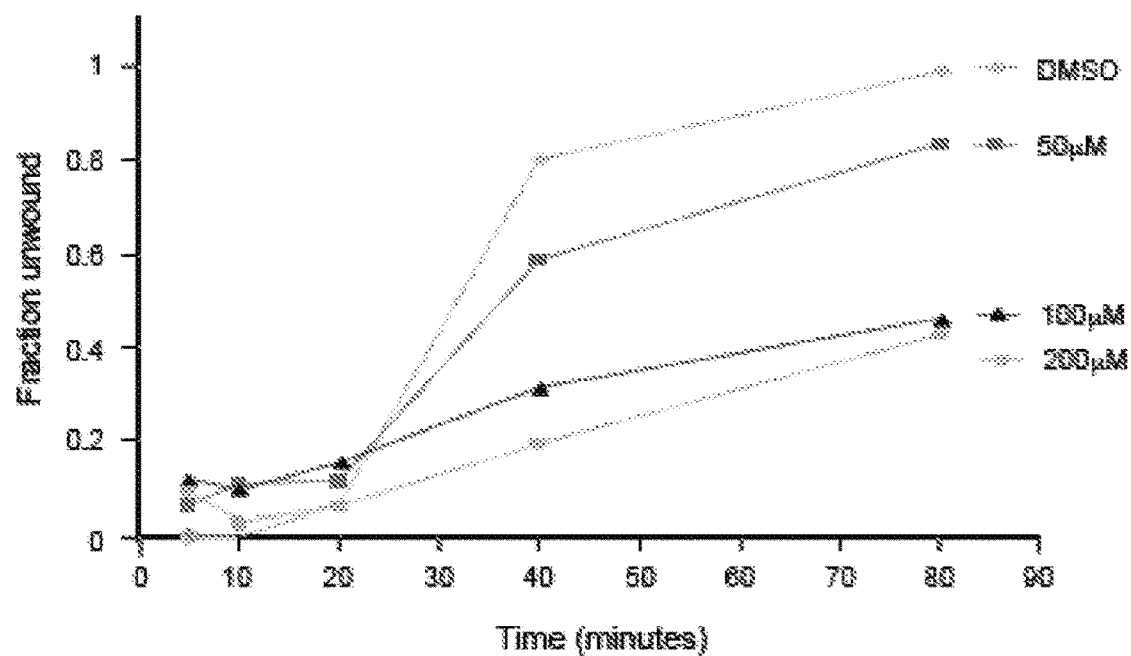
FIG. 5 is a chart showing Compound 3 inhibits helicase activity of DDX3.

Generating small molecular inhibitors of DDX3 function. As loss of DDX3 function abrogated colony forming abilities along with increased expression in lung carcinoma samples, a search was initiated to identify molecules that could target a functional substrate binding site of DDX3 protein. Initial work generated a fused diimidazodiazepine ring molecule (Compound 3) to target RNA helicase. To confirm the functional activity of Compound 3 on DDX3, an in vitro assay was carried out to determine the effects of Compound 3 on helicase activity. DDX3 protein was synthesized using the pET system from Novagen. Following DDX3 purification, the unwinding assays were performed using duplex oligos, purified DDX3 and Compound 3. Quantification was done by evaluating the pixel density of the native duplex oligos and the unwound oligos. As shown in FIG. 5, 100 μM of Compound 3 was able to reduce unwinding of the duplex oligos by at least 60% over a period of 80 minutes. This indicates that Compound 3 has the ability to inhibit the unwinding properties of DDX3.

Example 4

Figure 6:
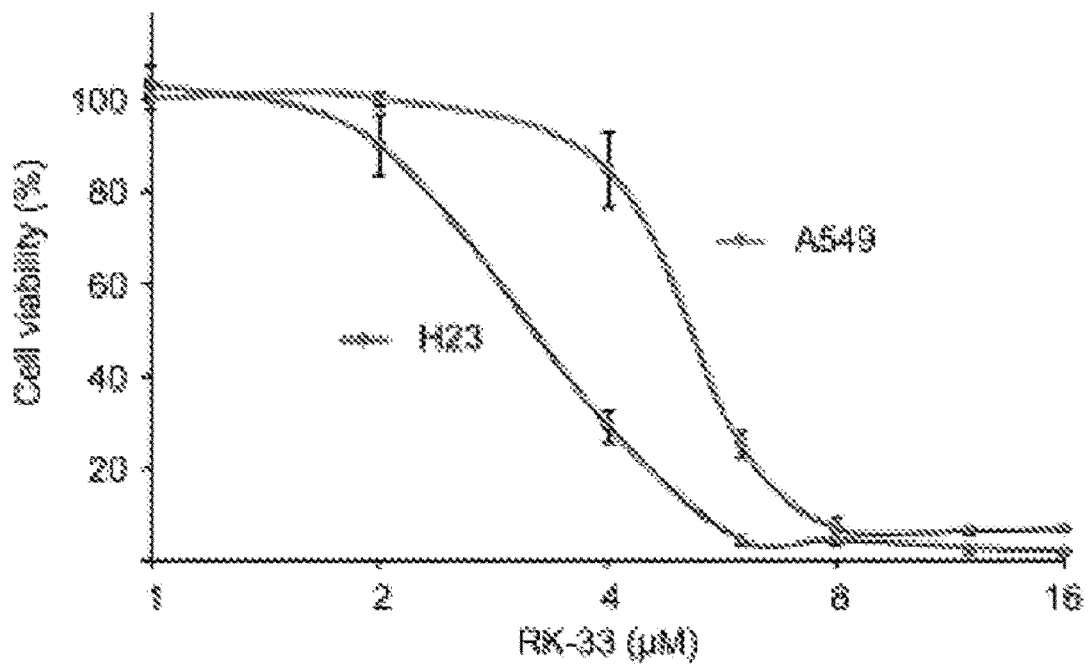
FIG. 6 is a plot showing the effect of Compound 3 on two lung cancer cell lines. Lung cancer cell lines were incubated with different concentrations of Compound 3. At day 3, MTS assays were performed to determine the percentage of metabolically active cells. The experiments were repeated in triplicate. The IC50 values for H23 and A549 are 3.5 and 5 μM respectively.
Figure 7:
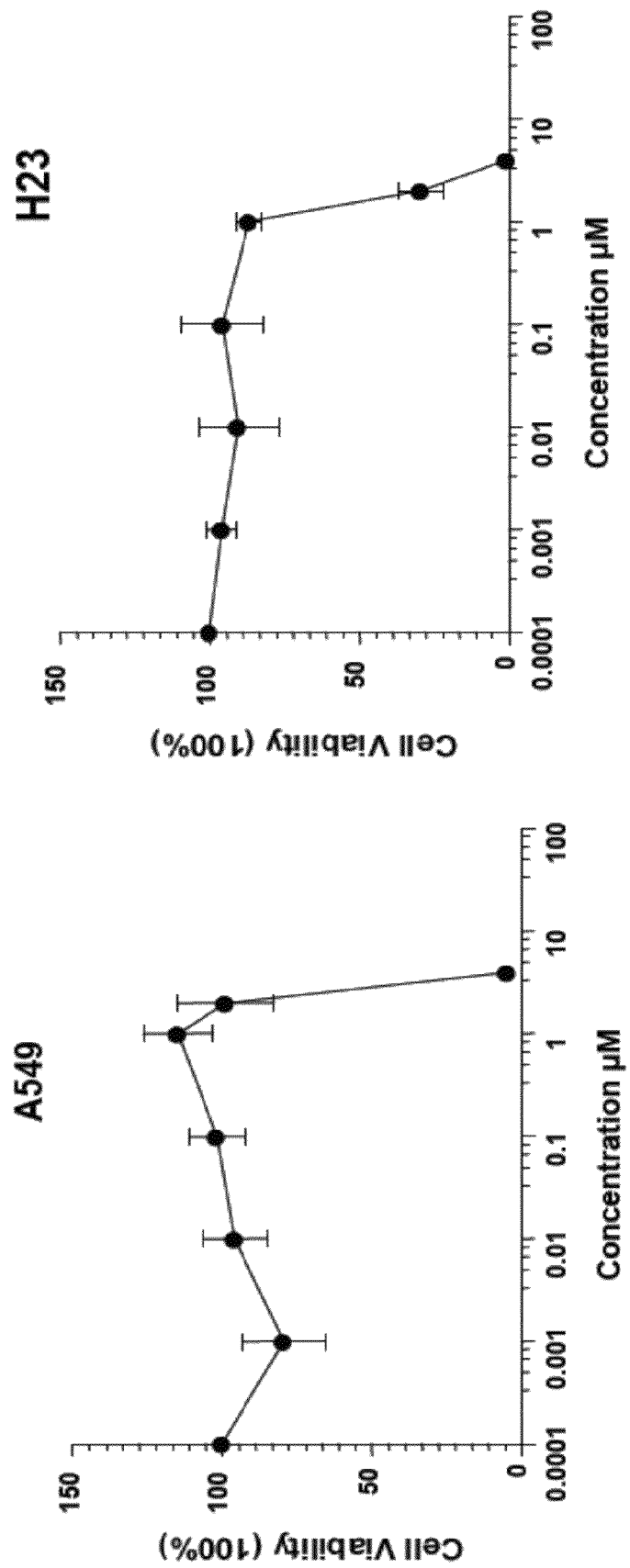
FIG. 7 illustrates the viability of lung cancer cell lines A549 and H23 when contacted with illustrative compound of the invention.

To study the effects of Compound 3 on cell growth and proliferation, lung cancer cell lines (H23 and A549) were used for the initial studies. As shown in FIG. 6, 8 μM of Compound 3 was able to efficiently ablate both the cancer cell lines. This is the first data set of evaluating the efficacy of a small molecule inhibitor of DDX3 to kill lung cancer cells. (See Also FIG. 7.)

Example 5

Figure 8:
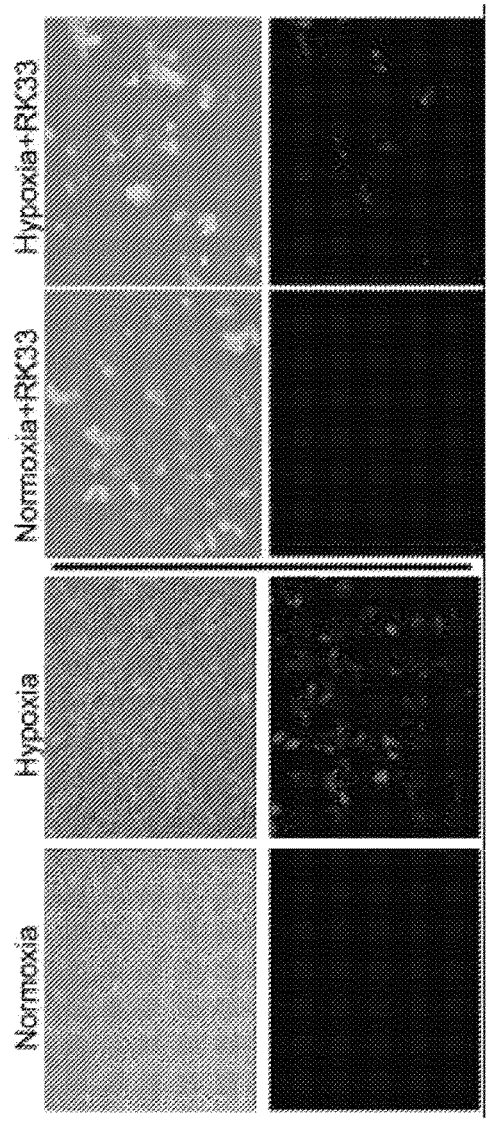
FIG. 8 shows that Compound 3 can induce cell death under hypoxic conditions. Cells engineered to express a hypoxia induced red fluorescent protein (tdTomato) were incubated with $CoCl_2$ (hypoxia mimetic compound) for 24 hours, following which Compound 3 was added and incubated for 72 hours. Photomicrographs were taken at 20×. Experiments were repeated twice.

Effect of hypoxia on the functional activity of Compound 3 to induce cell death. During solid tumor biogenesis, regions of hypoxia develop within the tumor due to inadequate and poorly formed vasculature. These regions have been shown to be resistant to chemo- and radio-therapy and have also been closely linked to malignant progression. In addition, some have posited that tumor hypoxia is a major limiting factor of the curability by SABR at lower radiation dose. Most of the current prescribed chemotherapeutic agents for cancer treatment exhibit inadequacy to induce cell death under hypoxic conditions. To evaluate efficacy of Compound 3 to induce cell death under hypoxic conditions, cells were incubated with $CoCl_2$ (hypoxia mimetic compound) for 24 hours, following which Compound 3 was added and incubated for 72 hours. As shown in FIG. 8, Compound 3 was able to retain its activity both under normoxic and hypoxic conditions, thus making it an excellent agent for cancer treatment in general.

Example 6

Figure 9:
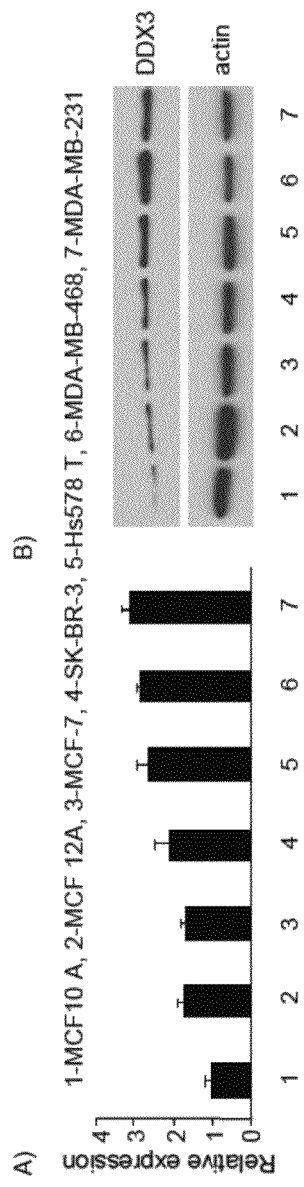
FIG. 9 illustrates DDX3 expression in normal breast cell lines (1-2) and a series of breast cancer cell lines (3-7)

The expression profile of DDX3 in breast cancer patient samples by qRT-PCR was studied in order to determine whether DDX3 is lost or over-expressed relative to tumor grade. FIG. 9A illustrates qRT-PCR of DDX3 levels in a series of immortalized normal breast cell lines (1-2) and breast cancer cell lines (3-7). The breast cancer cell lines are in the order of aggressive phenotype. FIG. 9B shows the immunoblot analysis for DDX3 expression in the same cell lines.

Figure 10:
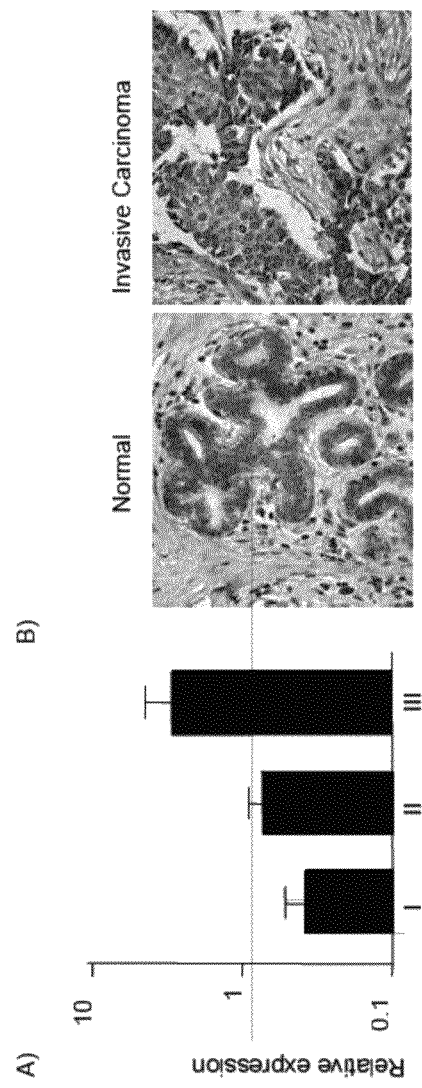
FIG. 10 illustrates qRT-PCR of DDX3 levels in different grades of human breast carcinoma samples (FIG. 10A) and immunostaining for DDX3 levels in normal mammary epithelium and primary breast carcinomas (FIG. 10B)
Figure 11:
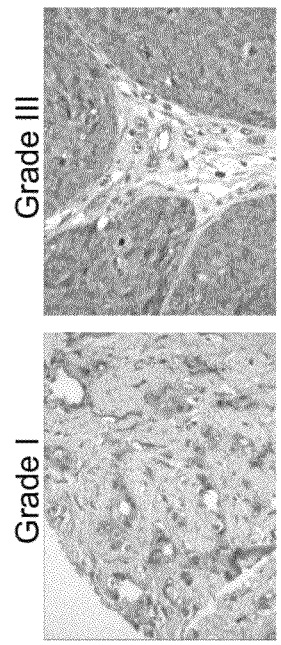
FIG. 11 illustrates representative photomicrographs of sections of breast tissue stained with DDX3-specific, affinity purified, rabbit polyclonal antibody.

As displayed in FIG. 10A, expression levels of DDX3 increase as tumors progress from grade 1 to grade 3. There is 1.9 fold increase in DDX3 mRNA levels in grade 2 tumors (14 samples) over grade 1 tumors (12 samples, P>0.05) and a 4-fold increase in DDX3 mRNA levels in grade 3 (13 samples) over grade 2 tumors (P<0.0001). The DDX3 mRNA levels were normalized with the basal levels of DDX3 from five normal breast tissue samples. (FIG. 10B shows immunostaining for DDX3 levels in normal human breast sections and in breast carcinoma sample.) This indicates that gain of DDX3 expression correlates with high-grade breast carcinoma samples and can be potentially used as a prognostic marker for breast cancer progression. Similar results were also obtained by immunohistochemistry on different grades of breast carcinomas. As shown in FIG. 11, grade III breast tumors have high cytoplasmic staining as compared to grade I. Also, comparison of 423 breast tumor samples indicated that high cytoplasmic DDX3 expression is associated with high mitotic index and high grade (P=0.05, data not shown). Both sets of data indicate a functional role for DDX3 in the pathogenesis of human breast cancer.

Example 7

Figure 12:
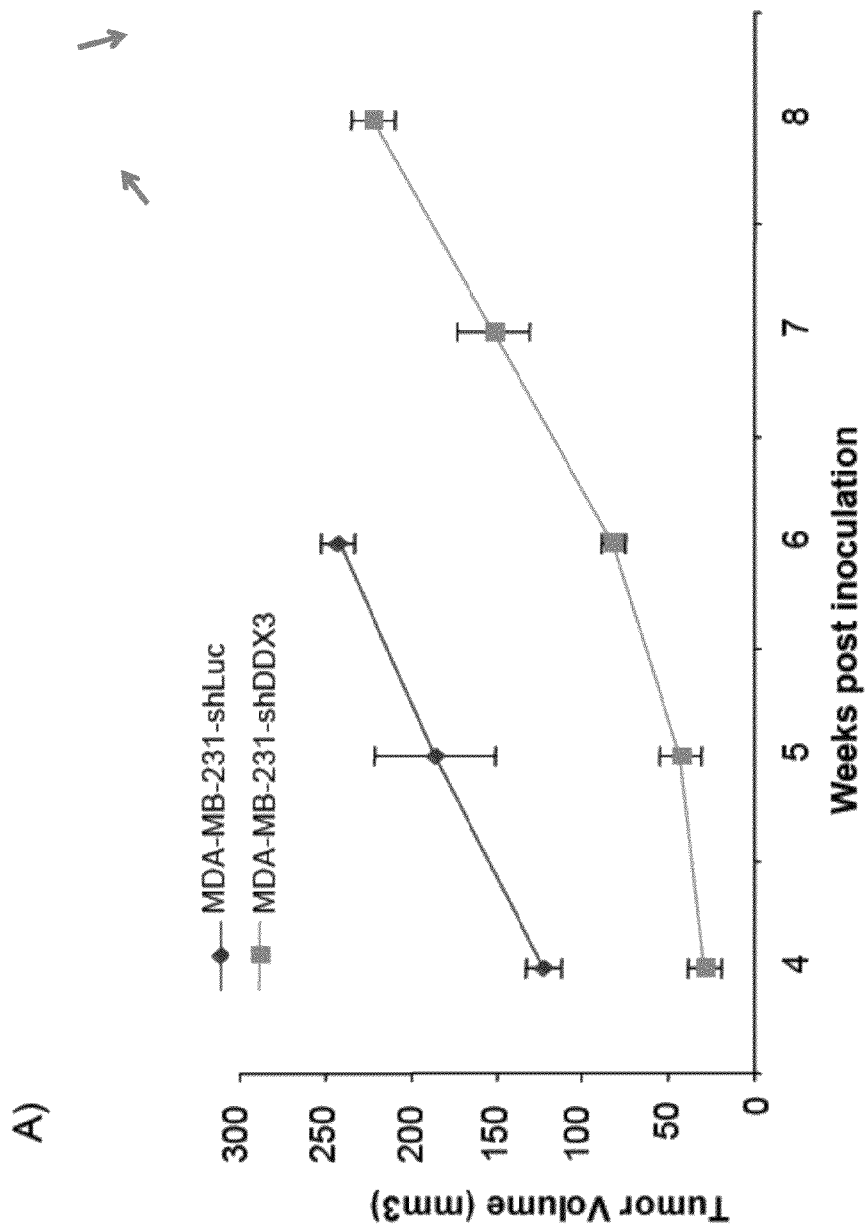
FIG. 12A is a graph showing tumor growth rate in the mammary fat pad of SCID mice (preclinical breast cancer model) using wild type and DDX3 knockdown MDA-MB-231 cells.
FIG. 12B shows photomicrographs of cross section of lungs of animals injected orthotopically (mammary fat pad) with MDA-MB-231 and MDAMB-231-shDDX3 cells.

Tumor growth rate in the mammary fat pad of SCID mice (preclinical breast cancer model) using wild type and DDX3 knockdown MDA-MB-231 cells is illustrated in FIG. 12A. FIG. 12B is photomicrographs of cross section of lungs of animals injected orthotopically (mammary fat pad) with MDA-MB-231 and MDA-MB-231-shDDX3 cells. Note that the lungs from MDA-MB-231-shDDX3 injected animals showed no tumor formation as compared to the wild type cells (black arrows points to lung metastasis).

Example 8

MTS Assays were used to evaluate the effective of compounds that downregulate DDX3 on viability in a number of different cell lines. In general, the CellTiter One Solution Assay (Promega) was used. The CellTiter One Solution Assay is a colorimetric method for determining the number of viable cells in proliferation or cytotoxicity assays. The One Solution contains MTS compound and an electron coupling reagent PES. The MTS compound is bioreduced by cells into a colored formazan product that is soluble in tissue culture medium. The quantity of formazan product as measured by the amount of 490 nm absorbance is directly proportional to the number of living cells in culture.

Procedure:
1. 25,000 cells were seeded in 24 well plate in duplicate for each concentration of Compound 3.
2. Twenty four hours after seeding, the medium was replaced with Compound 3 in fresh medium. Cells were incubated for 72 hrs. After completion of the treatment the media containing Compound 3 was replaced with MTS reagent. Culture medium "no-cell" control was used as a negative control at the same time.
3. Absorbance at 490 nm (450-540 nm) was measured using a plate reader. The absorbance values were subtracted from "no-cell" control, which yield the corrected absorbance.

Figure 13:
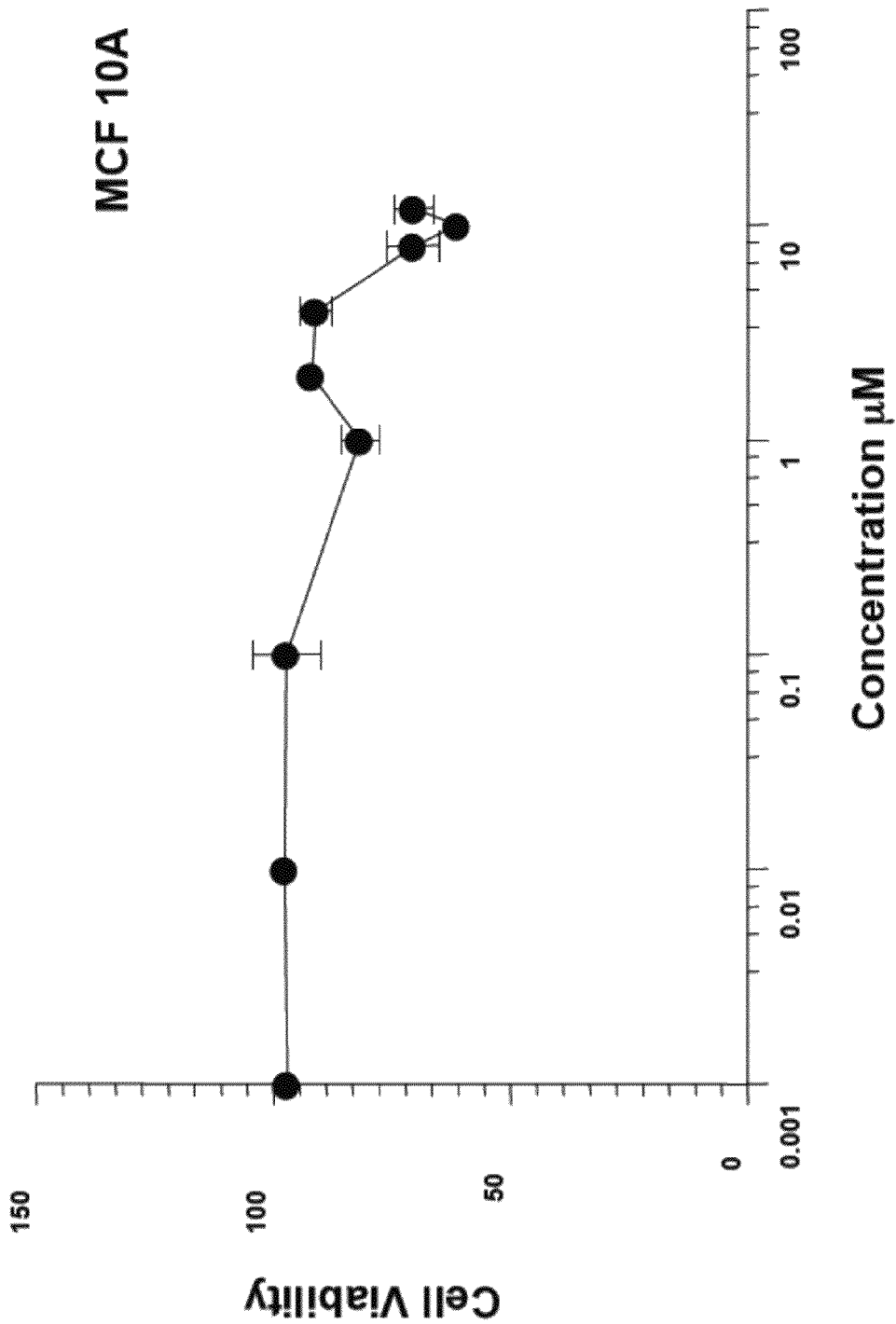
FIG. 13 illustrates MTS assays of MCF 10A cells (immortalized normal breast cell line) incubated with Compound 3 of the invention. X-axis indicates concentration of drug used. The cells were incubated for three days (fresh drug was added daily) following which cell viability was determined.

MTS assays of MCF 10A cells (immortalized normal breast cell line) incubated with Compound 3 are illustrated in FIG. 13. X-axis indicates concentration of drug used. The cells were incubated for three days (fresh drug was added daily) following which cell viability was determined.

Figure 14:
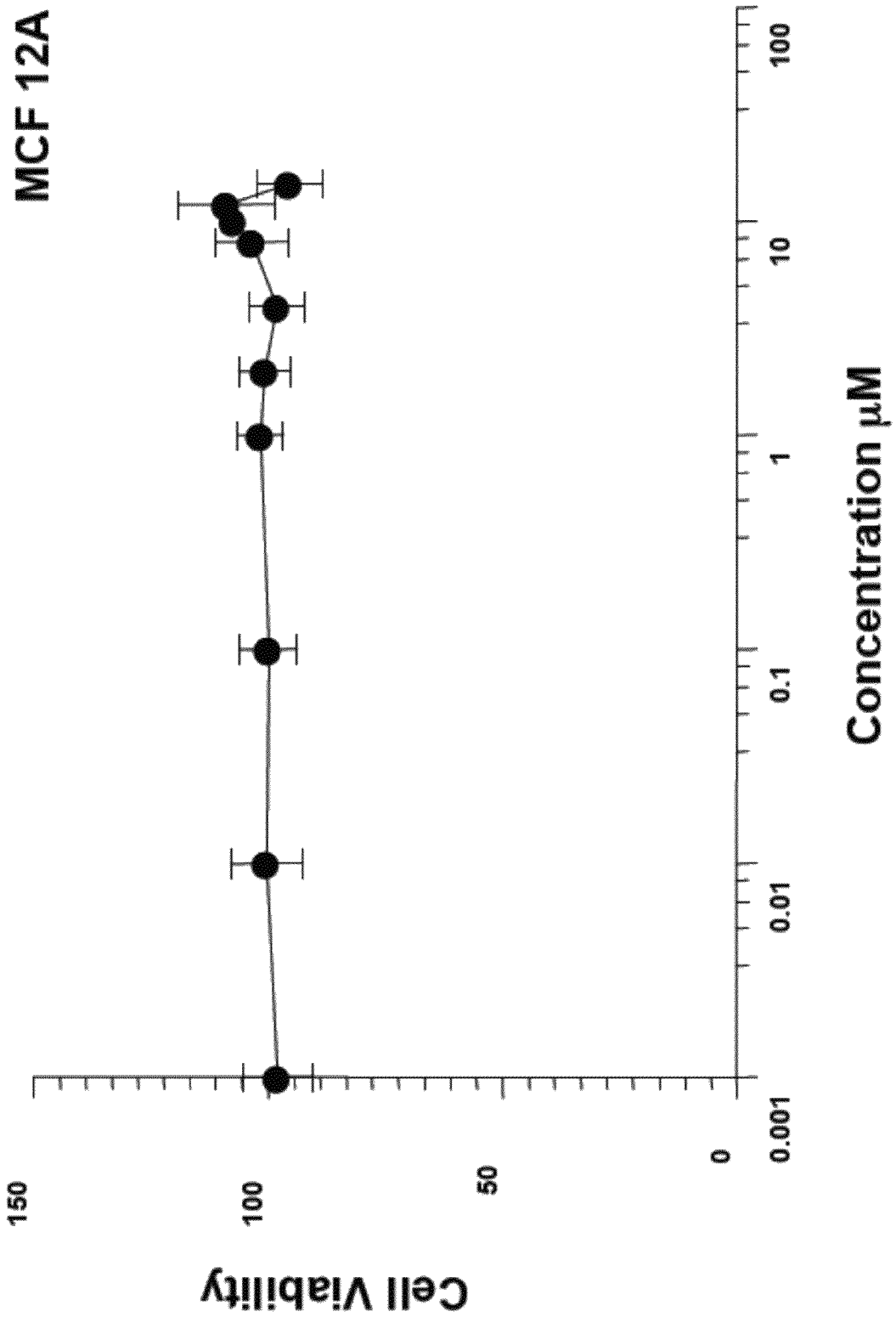
FIG. 14 illustrates MTS assays of MCF 12A cells (immortalized normal breast cell line) incubated with Compound 3 of the invention. X-axis indicates concentration of drug used. The cells were incubated for three days (fresh drug was added daily) following which cell viability was determined.

MTS assays of MCF 10A cells (immortalized normal breast cell line) incubated with Compound 3 are illustrated in FIG. 14. X-axis indicates concentration of drug used. The cells were incubated for three days (fresh drug was added daily) following which cell viability was determined.

Figure 15:
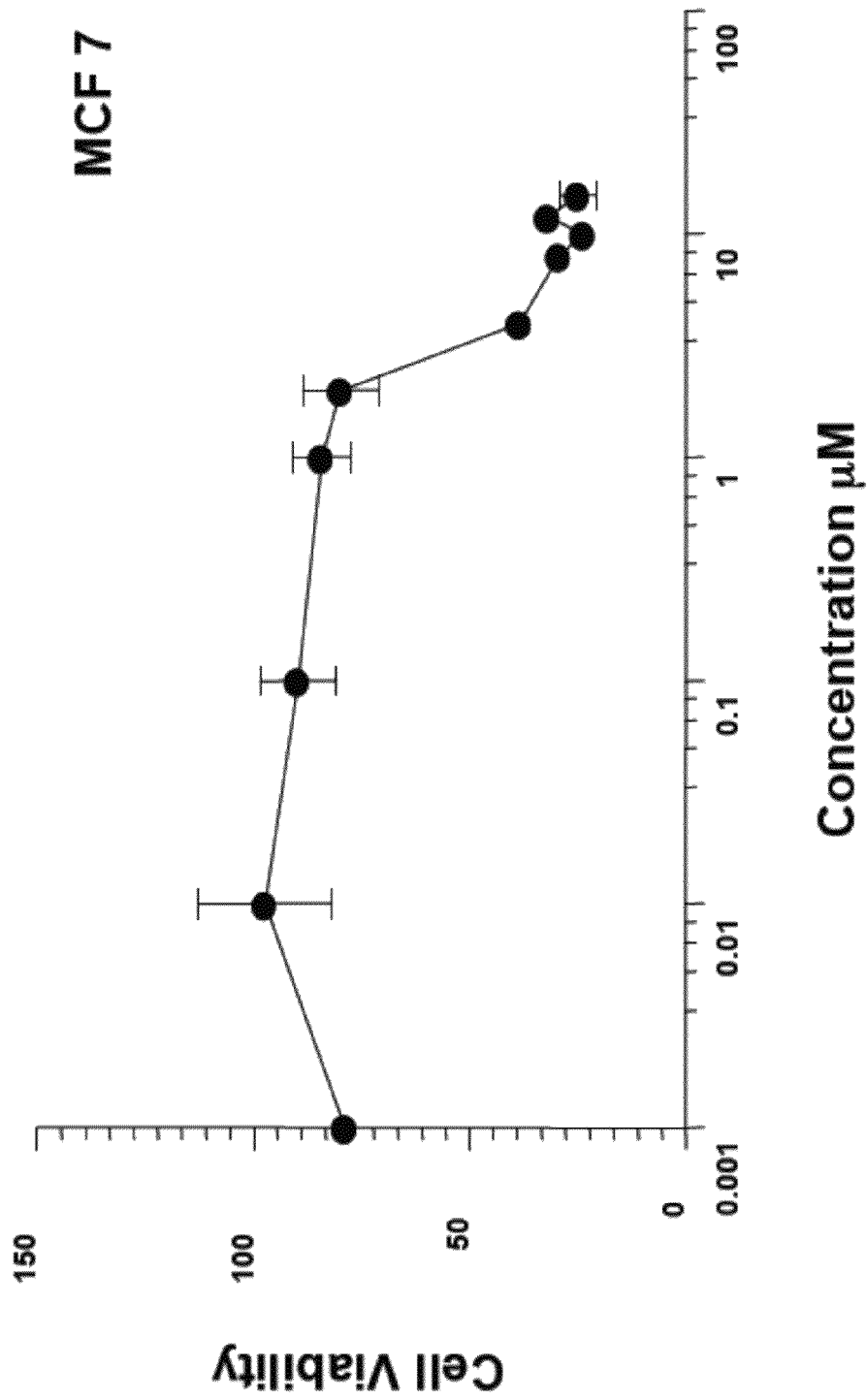
FIG. 15 illustrates MTS assays of MCF-7 cells (breast cancer cell line) incubated with Compound 3 of the invention.

MTS assays of MCF-7 cells (breast cancer cell line) incubated with Compound 3 are illustrated in FIG. 15. X-axis indicates concentration of drug used. The cells were incubated for three days (fresh drug was added daily) following which cell viability was determined.

MTS assays of MDA-MB-468 cells (breast cancer cell line) incubated with Compound 3 are illustrated in FIG. 16. X-axis indicates concentration of drug used. The cells were incubated for three days (fresh drug was added daily) following which cell viability was determined.

MTS assays of MDA-MB-231 cells (breast cancer cell line) incubated with Compound 3 are illustrated in FIG. 17. X-axis indicates concentration of drug used. The cells were incubated for three days (fresh drug was added daily) following which cell viability was determined.

MTS assays of HL60T cells (leukemia cell line) incubated with Compound 3 are illustrated in FIG. 18. X-axis indicates concentration of drug used. The cells were incubated for three days (fresh drug was added daily) following which cell viability was determined.

MTS assays of HNT34 cells (leukemia cell line) incubated with Compound 3 are illustrated in FIG. 19. X-axis indicates concentration of drug used. The cells were incubated for three days (fresh drug was added daily) following which cell viability was determined.

MTS assays of KG101 cells (leukemia cell line) incubated with Compound 3 are illustrated in FIG. 20. X-axis indicates concentration of drug used. The cells were incubated for three days (fresh drug was added daily) following which cell viability was determined.

MTS assays of U87 cells (glioblastoma human cell line) incubated with Compound 3 are illustrated in FIG. 21. X-axis indicates concentration of drug used. The cells were incubated for three days (fresh drug was added daily) following which cell viability was determined.

MTS assays of PC3 cells (prostate cancer cell line) incubated with Compound 3 are illustrated in FIG. 22. X-axis indicates concentration of drug used. The cells were incubated for three days (fresh drug was added daily) following which cell viability was determined.

Example 9

Prostate cancer samples stained for DDX3 expression showed robust DDX3 expression as compared to the normal prostate. In a patient cohort (n=90), a strong correlation was observed with DDX3 and cell proliferation biomarker Ki-67 (R=0.332; $p<0.001$), which has been shown to be significantly associated with survival in prostate cancer. Also, a trend of higher levels of DDX3 in 35% of tumors which were Gleason grade 7 or higher (OR=2.133) was observed and the staining intensity of DDX3 in normal vs. cancer cells (Gleason grade 7 or higher) was significant ($p<0.02$). This illustrates the role of DDX3 in the pathogenesis of human prostate cancer. Representative photomicrographs of normal tissue sections and prostate carcinoma tissue sections stained with DDX3 antibody are shown in FIG. 23.

Example 10

A total of 158 sarcoma samples (15 subtypes) were analyzed for DDX3 expression by IHC. The results were as follows:

| Sarcoma type (N) | Degree of DDX3 expression | | |
|---|---|---|---|
| | none | weak | moderate or strong |
| Angiosarcoma (9) | 0 | 7 | 2 |
| Chondrosarcoma (4) | 0 | 2 | 2 |
| Clear cell sarcoma (4) | 0 | 1 | 3 |
| Epithelioid sarc. (8) | 0 | 0 | 8 |
| ESFT/PNET (25) | 3 | 12 | 10 |
| Leiomyosarcoma (13) | 0 | 9 | 4 |
| Low-grade sarcoma (3) | 0 | 2 | 1 |
| Sarcoma type (N) | | | |
| Liposarcoma (12) | 0 | 2 | 10 |
| MFH (17) | 0 | 6 | 11 |
| MPNST (4) | 0 | 2 | 2 |
| Myxoid sarcomas (19) | 0 | 11 | 8 |
| Kaposi's sarcoma (27) | 2 | 8 | 17 |
| Pleo. sarcoma (5) and fibrosarcoma (1) | 0 | 1 | 5 |
| RMS (7) | 0 | 4 | 3 |

As shown above, only 5 samples (3%) had no DDX3 expression. Eighty-six samples (54%) had moderate to strong expression, and 67 samples (42%) had weak expression. Exemplary photomicrographs (chondrosarcoma and pleomorphic sarcoma tissue sections) stained with DDX3 antibody are illustrated in FIG. 24.

Example 11

DDX3 expression was investigated by IHC in brain tumors. FIG. 25 shows exemplary photomicrographs of normal brain tissue, glioblastoma and medulloblastoma. As shown in FIG. 25, glioblastoma and medulloblastoma exhibit increased expression of DDX3 as compared to normal brain tissue.

Example 12

In order to determine expression of DDX3 in various cancer cell lines, immunoblot analyses were undertaken and compared to normal cell lines. FIG. 24 illustrates immunoblot analyses for DDX-3 expression in normal lung cell line (AEF), lung cancer cell lines (H-23 and A546), prostate cancer cell line (PC-3) and glioblastoma cancer cell line U87).

Example 13

Figure 30:
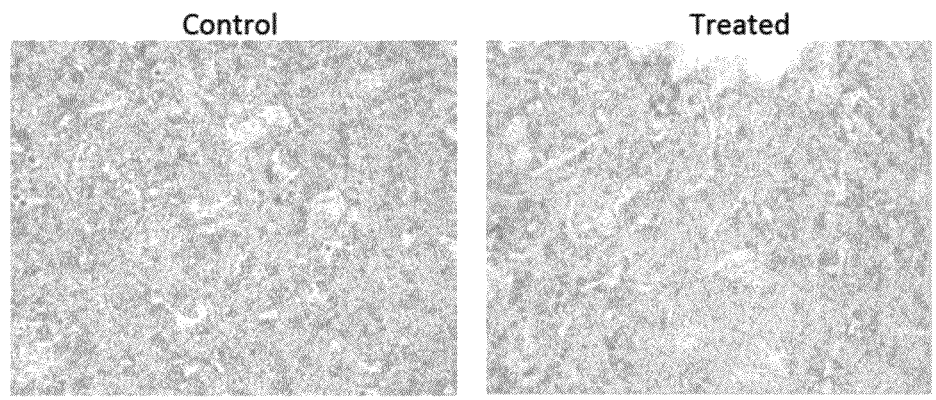
Figure 31:
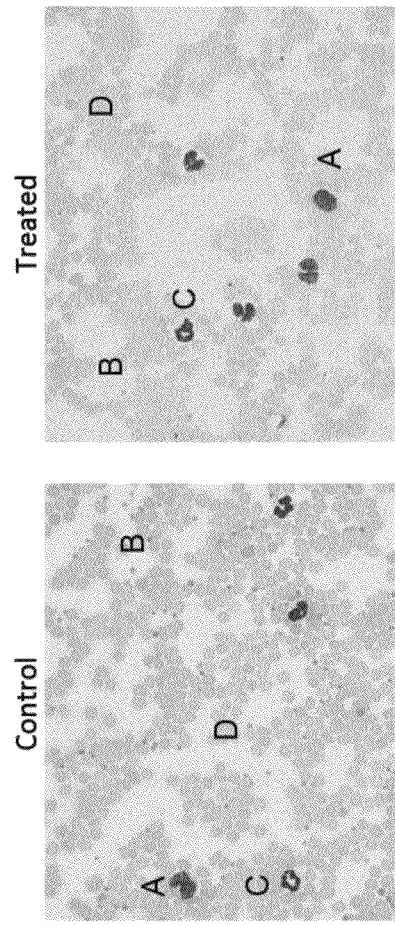

Analysis of the toxicity of Compound 3 was conducted in SCID mice. FIGS. 25-29 show tissue samples in control and untreated samples of brain (cerebellum), kidney, Liver, spleen, and blood, respectively. Data shown is that of 500 µM of Compound 3 of the invention that were injected twice daily for four weeks. Following that the drug was injected once a week for three weeks. At the end of the experiment the animals were sacrificed and histopathology performed. The range of drug dose tested was from 500 to 100 µM. An extensive pathological examination of all tissues was performed following necropsy, which indicated no tissue damage. Subsequently, we carried out pharmacokinetics in multiple tissue compartments. For this a LC/MS/MS method was developed for determination of Compound 3 in mouse plasma (FIG. 30-inset). Sample preparation involved acetonitrile precipitation and separation of Compound 3 and the internal standard, temazepam, was achieved on a Waters Xterra column. As indicated in FIG. 30, brain exposures are well managed and target tissues are well above effective killing concentrations. The animals were injected I.P. (single dose of 20 mg/kg with five animals per arm) and the tissue harvested at different time intervals (30 minutes, 60 minutes and 24 hours) and analyzed.

The results confirm that the illustrative compounds of the invention were successful in killing cancer cell lines while at the same time not affecting normal cells.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method of treating a hyperproliferative disorder susceptible to treatment by downregulation of DDX3 comprising administering to a subject in need thereof an effective amount of a composition or formulation comprising a compound of Formula (IV), wherein such compound downregulates DDX3, and wherein the compound of Formula (IV) is:

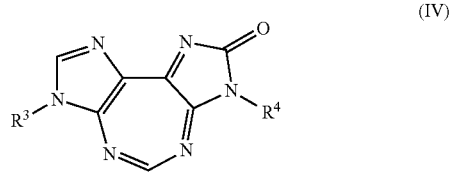

or pharmaceutically acceptable salts and prodrugs thereof, wherein:

$R^3$ and $R^4$ are each independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, benzyl group, cyclic or acyclic heteroalkyl group, heteroaryl group.

2. The method of claim 1, wherein the compound is

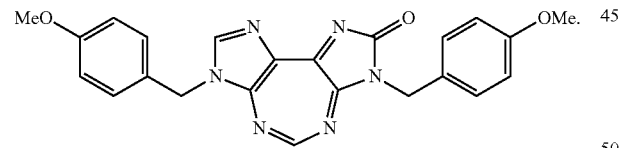

3. The method of claim 1, wherein the hyperproliferative disorder is selected from the group consisting of group consisting of breast cancer, lung cancer, prostate cancer, glioblastoma, kidney cancer, leukemia, medulloblastoma, pontine tumors, or a sarcoma.

4. The method of claim 1, wherein the hyperproliferative disorder is selected from the group consisting of breast cancer, lung cancer, prostate cancer or glioblastoma.

5. The method of claim 1, wherein the hyperproliferative disorder is breast cancer.

6. The method of claim 1, wherein the hyperproliferative disorder is lung cancer.

7. The method of claim 3, wherein the sarcoma is selected from the group consisting of chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS).

8. A method of treatment of a subject having a hyperproliferative disorder susceptible to treatment by down regulation of DDX3 comprising:
   a) obtaining a cell or tissue sample from tissue of the subject associated with or suspected to be associated with the disorder;
   b) optionally isolating cells from the tissue;
   c) measuring expression of DDX3 in the tissue or in the cells isolated from the tissue using qRT-PCR and PCR primers and probes specific for DDX3, or using immunohistochemistry and antibodies specific for DDX3 or an antigen binding fragment thereof;
   d) providing a reference non-neoplastic tissue sample;
   e) comparing expression level of the DDX3 gene from the tissue sample of the subject, to expression level of the DDX3 gene in a reference non-neoplastic tissue sample;
   f) identifying the subject as having the hyperproliferative disorder as susceptible to treatment by down regulation of DDX3 if DDX3 is expressed at an increased level in the tissue or cell sample of the subject when compared to the reference non-neoplastic tissue sample; and
   g) administering to the subject an effective amount of a composition or formulation comprising a compound of Formula (IV), wherein such compound downregulates DDX3, and wherein the compound of Formula (IV) is:

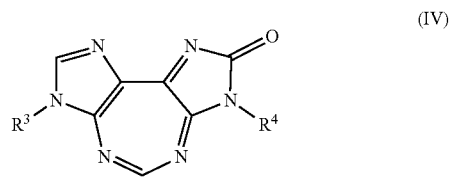

or pharmaceutically acceptable salts and prodrugs thereof, wherein:

$R^3$ and $R^4$ are each independently a hydrogen; hydroxyl; substituted or unsubstituted: cyclic or acyclic alkyl group, cyclic or acyclic alkenyl group, cyclic or acyclic alkynyl group, aryl group, alkylary group, aryalkyl group, benzyl group, cyclic or acyclic heteroalkyl group, heteroaryl group.

9. The method of claim 8, wherein the hyperproliferative disorder is selected from the group consisting of breast cancer; lung cancer; prostate cancer; brain cancer including glioblastoma, medulloblastoma, and pontine tumors; kidney cancer; leukemia; or a sarcoma.

10. The method of claim 8, wherein the hyperproliferative disorder is selected from the group consisting of breast cancer, lung cancer, prostate cancer or glioblastoma.

11. The method of claim 8, wherein the hyperproliferative disorder is breast cancer.

12. The method of claim 8, wherein the hyperproliferative disorder is lung cancer.

13. The method of claim 9, wherein the sarcoma is selected from the group consisting of chondrosarcoma, malignant fibrous histiocytoma (MFH), clear cell sarcoma, malignant peripheral nerve sheath tumor (MPNST), epithelioid sarcoma, myxoid sarcomas, Ewings Sarcoma (ESFT or PNET), Kaposi's sarcoma, leiomyosarcoma, pleomorphic sarcoma, fibrosarcoma, low-grade sarcoma and rhabdomyosarcoma (RMS).

14. The method of claim 8, wherein measuring comprises immunohistochemistry analysis of the tissue sample.

15. The method of claim 8, further comprising isolating cells from the tissue sample and measuring expression of DDX3 in the tissue comprises measuring expression of DDX3 in the cells.

16. The method of claim 15, further comprising performing an assay by exposing the cells to a compound that down-regulates DDX3, measuring cell viability as a function of concentration and identifying the hyperproliferative disorder as susceptible to treatment by down regulation of DDX3 if cell viability decreases as a function of concentration.

17. The method of claim 16, wherein the assay comprises a MTS assay.

18. The method of claim 16, wherein the compound is

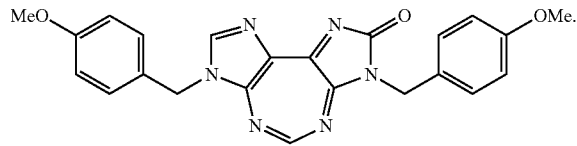 [SMILES: COc1ccc(Cn2c3ncnc4c(ncn4Cc4ccc(OC)cc4)c-3nc2=O)cc1]

19. The method of claim 1, wherein $R^3$ and $R^4$ are benzyl, optionally substituted with —F, —Cl, —Br, —I, —OH, azido, —SH, alkyl, aryl, heteroalkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, or triazolyl.

20. The method of claim 1, wherein $R^3$ and $R^4$ benzyl, optionally substituted with —F, —Br, —OMe, —Cl, —$NO_2$, —I, —$N(CH_3)_2$, —OH, —$N_3$, -Ph, —NHOH, —$NH_2$, —$NHCH_3$, —SH, -Me, —$SCH_3$, —COPh, triazole, —CO$(CH_2)_X CH_3$, —O$(CH_2)_Y CH_3$, wherein X is from 1 to 17 and Y is from 1 to 10.

21. The method of claim 8, wherein $R^3$ and $R^4$ are benzyl, optionally substituted with —F, —Cl, —Br, —I, —OH, azido, —SH, alkyl, aryl, heteroalkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, or triazolyl.

22. The method of claim 8, wherein $R^3$ and $R^4$ benzyl, optionally substituted with —F, —Br, —OMe, —Cl, —$NO_2$, —I, —$N(CH_3)_2$, —OH, —$N_3$, -Ph, —NHOH, —$NH_2$, —$NHCH_3$, —SH, -Me, —$SCH_3$, —COPh, triazole, —CO$(CH_2)_X CH_3$, —O$(CH_2)_Y CH_3$, wherein X is from 1 to 17 and Y is from 1 to 10.

* * * * *